United States Patent [19]
Spiess

[11] Patent Number: 5,271,230
[45] Date of Patent: Dec. 21, 1993

[54] LIQUID GAS TEMPERATURE CONTROL APPARATUS FOR AND METHODS OF DEPRESSING TEMPERATURE TO AND MAINTAINING IT AT A CHOSEN DEPRESSED VALUE

[75] Inventor: Lewis H. Spiess, Oxfordshire, England

[73] Assignee: Perkin-Elmer Ltd., Beaconsfield, England

[21] Appl. No.: 748,715

[22] Filed: Aug. 22, 1991

[30] Foreign Application Priority Data

Sep. 6, 1990 [GB] United Kingdom ............... 9019485

[51] Int. Cl.$^5$ .................................................. F17C 7/02
[52] U.S. Cl. ..................................... 62/3.6; 62/223;
62/504; 62/64; 62/56; 62/50.1
[58] Field of Search ............... 62/50.1, 50.2, 50.4,
62/223, 332, 3.61, 3.6, 51.2

[56] References Cited

U.S. PATENT DOCUMENTS

| | | | |
|---|---|---|---|
| 3,271,970 | 9/1966 | Berner | 62/223 |
| 3,315,474 | 4/1967 | Farer | 62/3.61 |
| 3,512,370 | 5/1970 | Murphy et al. | 62/332 |
| 3,705,500 | 12/1972 | Jehle | 62/223 |
| 3,714,793 | 2/1973 | Eigenbrod | 62/50.2 |
| 4,041,725 | 8/1977 | Garside | 62/223 |
| 4,576,010 | 5/1986 | Windecker | 62/51.2 |

*Primary Examiner*—John M. Sollecito
*Attorney, Agent, or Firm*—Edwin T. Grimes

[57] ABSTRACT

Apparatus and methods are disclosed for lowering the temperature within a chamber from a higher actual value to a set desired lower value, the latter being stabilized by intermittently flowing liquid gas selectively through the chamber and a venting orifice, under the control of a microcomputer responding to a temperature sensor within the chamber. In one embodiment (FIG. 2), the chamber (2) and the venting orifice (11B) is supplied with coolant through separate solenoid valves (1,5) which are both open to allow maximum coolant flow rate during the initial cool-down and during the settling down stage and the approach to the steady state which follow operate with much reduced coolant flow in a coordinated intermittent mode wherein the venting orifice valve (5) is open only when extra cooling is momentarily required to assist the action of the valve (1) supplying the chamber.

39 Claims, 9 Drawing Sheets

LIQUID GAS TEMPERATURE CONTROL APPARATUS FOR AND METHODS OF DEPRESSING TEMPERATURE TO AND MAINTAINING IT AT A CHOSEN DEPRESSED VALUE

BACKGROUND OF THE INVENTION

This invention relates to temperature control, both in terms of systems and methods, intended for lowering the temperature of an enclosure or partial enclosure and/or any objects within it from a higher actual value to a desired lower value and maintaining it substantially constant at the desire lower value for any required periods by flowing through the enclosure a liquefied gas in either the liquid or the vaporized state as the application demands. The cooling effect of the liquefied gas, which is drawn from a suitable storage container, is determined by controlling the rate at which it flows through the enclosure and the rate at which it is dissipated, e.g. to atmosphere, via a venting orifice, the two rates being so coordinated in response to the temperature sensed within the enclosure as to attain and -maintain the desired lower temperature.

In the present specification, the term "lower" in the phrase "the desired lower temperature", or the equivalent phrase "the desired lower value" following a prior mention of the term "temperature", shall be construed with reference to an assumed "actual higher temperature", e.g. if an object is at 50° C. and it is required to cool it down to 5° C., the former value is the "actual higher temperature" and the latter the "desired lower temperature". The use of a liquefied gas coolant does not necessarily mean that the desired lower temperature is a sub-zero temperature.

A commercially available liquefied gas is usually referred to by the name of the gas preceded by the term "liquid", e.g. liquid helium. This convention will be followed in the present context and, by extension, the phrase "liquid gas" will be used as a generic expression to refer to liquefied gas either in the liquid or vaporized state, unless the context specifies one of the two states.

Liquid nitrogen, which is readily available at a comparatively low cost, is particularly suitable as a cooling medium (hereinafter coolant) in many applications where the temperature of the enclosure and/or any objects within it must be depressed down to $-100°$ C. or lower from a higher temperature; but even where the desired lower temperatures are not extreme, or, indeed, are above zero, liquid gas cooling may be indicated if high cool-down rates are required. If both high rates and very low temperatures must be attained, there are almost no practical alternatives, especially if high thermal capacitances are also involved.

In what follows specific reference will be made to liquid nitrogen as a coolant, but that shall not detract from the generality of suitable liquid gases that could be used as alternative coolants.

A problem encountered with liquid gas cooling is how to maintain a desired lower temperature within reasonably close limits, say, 1° C., when virtually the only expedient form of control is achieved by regulating the flow of the coolant, which flow is itself subject to variables, some of which are unpredictable. Before dwelling on the problem, it may be helpful to review briefly the construction of the vessel in which liquid gases are commercially supplied.

If we do take liquid nitrogen as an example, this product is made available commercially in a rather large stainless steel storage container called a Dewar (hereinafter the Dewar) which comprises an inner cylinder suspended from its top end within and spaced from an outer cylinder, the interspace being evacuated for good thermal insulation in order to minimize heat flow from ambient and keep vaporization of the liquid nitrogen within acceptable limits. In a typical arrangement, a manifold into which are screwed taps is provided at the top of the Dewar: one, the supply tap, communicates with a long narrow pipe reaching close to the bottom of the inner cylinder and is intended for supplying liquid nitrogen to a utilization circuit; the other communicates with a short pipe which only reaches just beyond the upper end wall of the inner cylinder and serves to draw vaporized liquid nitrogen instead, if so required by the user, apart from enabling the user to pressurize the Dewar with nitrogen gas to a pressure between 20 and 25 p.s.i. (i.e. between approximately 137 and 172 Kilopascals), unless self-pressurization has been provided for by the manufacturer of the Dewar. The pressure exerted by the vaporized liquid gas within the Dewar which bears on the liquid gas and forces it up the long pipe towards the supply tap shall hereinafter be referred to as Dewar pressure. A blow-off valve venting to atmosphere prevents any excess pressure building up. The user may in addition reduce the Dewar pressure by venting the coolant through the second mentioned tap. When the Dewar is not being used, some vaporized gas will be relieved from time to time, the frequency depending on ambient temperature, setting of the blow-off valve and Dewar insulation.

For the purpose of conveying liquid gas from the supply tap of the Dewar to a connection with the utilization circuit, a thermally insulated pipe of suitable length and bore is used that is usually referred to as a "transfer line". If the coolant in the transfer line has been static or flowing at a low rate for some time, the coolant will be in the vaporized state because under such conditions the cooling will not be adequate to maintain the liquid state against the warming effect on the coolant of ambient heat leaking through the thermal insulation of the transfer line. It follows that after first opening the supply tap of the Dewar the coolant may issue from the transfer line in the vaporized state until an appropriate coolant rate has been maintained long enough to cool down the transfer line to the point where vaporized gas is replaced by liquid gas. Naturally, the time required for the change over will depend on the flow rate. In fact, in all but the most demanding applications it is possible to switch over to vaporized liquid gas cooling by so adjusting the coolant rate that at a given ambient temperature it just fails to cool the transfer line sufficiently to effect the change over.

The transfer line may be supplied by the manufacturer of apparatus in which liquid gas cooling is utilized. Its characteristics will therefore be such as to allow the coolant flow rate to reach the maximum value likely to be required at the point of connection to the utilization circuit, assuming a standard Dewar pressure, such as between 20 and 25 p.s.i.. Of course, non-standard transfer lines and Dewar pressures may be substituted if desired and the coolant flow rate adjusted accordingly.

It will be appreciated from the above background details that cooling an enclosure requires a flow of coolant to be maintained through the enclosure. If we assume that a given maximum flow rate will be required to achieve a reasonably fast initial cool-down to the lowest temperature in the design range of a cooling system, that flow rate may be maintained continuously until the required temperature has been attained and thereafter on an intermittent basis via controlling means responsive to a temperature sensor within the enclosure, said means being adapted to ensure that the cooling effect is just adequate to balance the effect of heat transfer from ambient.

In a typical known arrangement, the coolant is passed through a solenoid valve which is either fully open or fully closed, depending on a command signal responsive to the temperature sensor. When the enclosure is at ambient temperature and the desired lower temperature is many tens of degrees below zero, the command signal causes the solenoid valve to stay open until the desired lower temperature is reached, when the solenoid valve begins to act intermittently.

Clearly, if a rapid cool-down to a very low temperature is required, the maximum flow rate must be comparatively high and yet when the low temperature has been reached the cooling effect required to maintain it is relatively small. To decrease the effect sufficiently, the solenoid valve must be operated at a very high rate of intermittence, which limits its life very considerably, affords poor temperature control, is inefficient in terms of coolant consumption and gives rise to objectionable noise. These are serious drawbacks of the prior art.

SUMMARY OF THE INVENTION

The object of the present invention is to provide temperature control systems and methods utilizing liquid gas as a coolant for lowering the temperature within a complete or a partial enclosure and/or the temperature of any objects therein from a higher actual value to a desired lower value which are characterized by smaller consumption of coolant, closer approximation to the set desired lower temperature, less noise, and less wear and tear of the controlling parts compared with known systems and methods.

The said object is essentialy achieved by providing two electrically operated coolant valves instead of the customary single valve, one valve being a coolant supply valve and the other a coolant venting valve, through which valves the flow of coolant is metered to the enclosure and a venting orifice, respectively, a microcomputer coordinating the operation of the valves.

In accordance with a broad aspect of the present invention there is provided a temperature control system for lowering the temperature within a chamber from a higher actual value to a desired lower value and maintaining it at said desired lower value by passing through the chamber a controlled flow of coolant available from a source of supply in the form of liquid gas, comprising:

a) a chamber adapted to allow a flow of coolant therethrough;

b) means for automatically selectively supplying coolant to the chamber and a venting orifice;

c) a temperature sensor located within the chamber;

d) a temperature setting means for setting the desired lower temperature;

e) a controller responsive to the temperature sensor and to the temperature setting means for controlling the means for automatically selectively supplying the coolant in order to bring the chamber and/or any object therein to and maintain it at the set desired lower value.

The term chamber in so far as the present invention is concerned shall refer to means for partially or totally enclosing a given space that is to be cooled to a desired lower temperature together with any object or objects located therein.

Where the desired temperature control is particularly demanding and the circumstances of the application permit it, the chamber may be located within an ante-chamber which is intermediate between ambient and the chamber and is itself subjected to cooling, the coolant being arranged to flow first through the chamber proper and then through the ante-chamber. The temperature within the chamber can then be controlled to fine limits because that of the surrounding ante-chamber does not greatly differ from it and thus acts as a particularly effective buffer against ambient temperature variations.

It shall be understood that in cooling an object within the chamber to a desired low value, the temperature of the object need not track that of the chamber, such as when the temperature sensor is in close thermal contact with the object.

In this context the phrase "coolant circuit" shall refer to the means through which the coolant is conveyed from the transfer line terminal for the purpose of lowering the temperature of the chamber to a desired lower value. Although strictly speaking the transfer line is not part of the "coolant circuit" in a system in accordance with the present invention, its characteristics are taken into account in the design and control of the coolant circuit.

In a first embodiment of the present invention, particularly suitable for cooling a chamber of low volume and/or low thermal capacity to a desired lower temperature by flowing therethrough vaporized liquid gas, the means for automatically selectively supplying coolant to the chamber and the venting orifice may comprise electrically controllable coolant supply valve and coolant venting valve, each having an input port and an output port.

The input port of the coolant supply valve may be adapted for receiving a liquid gas coolant from a supply Dewar through a transfer line and the output port may be connected to a coolant supply duct for conveying coolant to the chamber.

A coolant venting duct may be provided branching from the coolant supply duct and leading to the input port of the coolant venting valve, the output port of which either inherently or through an extension therefrom provides the venting orifice.

The controller may include a micro-computer responsive to dedicated software in determining the opening and closing of the two valves, each of which may be solenoid operated.

The micro-computer may be so conditioned by the software that during the initial cool-down of the chamber from the higher actual temperature to the desired lower temperature both the coolant supply valve and the coolant venting valve are kept open.

The impedance to coolant flow of the coolant supply duct and the coolant venting duct may be so arranged, in relation to given Dewar pressure and transfer line impedance, that the flow rate of coolant is just adequate for the initial cool-down of the chamber to the lowest temperature in the design range to be effected in an acceptable time. The flow rate may be chosen to ensure that the coolant is in the vaporized state. Alternatively, a higher flow rate may be used to cause the coolant to flow in the liquid state for a shorter cool-down time.

It should be observed that where the coolant is in the vaporized state the initial cool-down of the chamber takes advantage of the cumulative effect of coolant flow through the supply valve and the venting valve. Although the flow through the venting valve tends to reduce the flow through the chamber, it in fact causes the coolant to be delivered to the chamber at a temperature lower than would otherwise be the case, with the result that the valves actually cooperate in depressing the temperature of the chamber at a satisfactory rate.

The end of the initial cool-down period is reached when the temperature within the chamber, or of any object to be cooled therein, as the case may be, has dropped to the desired lower value. However, when that happens the transfer line, as well as the parts such as the coolant supply duct, the coolant venting duct, and the two respective valves which together with the chamber make up the coolant circuit, lag behind at a higher temperature. This is due to the fact that the thermal transfer rate from and to the coolant is likely to be much lower at least in some of said parts than in the chamber, wherein said rate is readily optimized. It follows that there could be considerable time lag before the temperature control system as a whole approximated thermal equilibrium, the part of the coolant circuit suffering the lower transfer rate finally determining the extent of the delay.

It may therefore be arranged, through the software, for the coolant supply valve to be kept open during the time the temperature control system is settling down towards thermal equilibrium following the initial cool-down in order to prevent some of the heat stored in the thermal capacity of the parts referred to from being dumped into the chamber and causing the temperature therein to rise. On the other hand, the full cooling effect may now be reduced to ensure that the temperature of the chamber does not fall below the desired lower value. This may be taken care of by arranging (again, through the software) for the coolant venting valve to be closed and perhaps re-opened occasionally to combat incidental temperature rises during the settling down process.

As thermal equilibrium is approached, the intervention of the venting valve will be for shorter and shorter periods, until at or near equilibrium it may be arranged, through the software, for the supply valve to take over control and operate intermittently so as just to compensate for heat leakage from ambient into the chamber. Occasional temperature disturbances causing the temperature to rise in the chamber may be counteracted whenever they occur, the software being made to provide for the momentary opening of the venting valve to augment the total coolant flow.

In the embodiment as outlined so far, the flow rate of the coolant is preferably chosen so as to ensure that the coolant will never enter the coolant circuit in the liquid state. It has been found that the use of coolant in the vaporized state enables the desired lower temperature to be controlled to closer limits that would be possible by flowing the coolant in the liquid state.

It will be appreciated that the two-valve control as outlined in the present embodiment lessens the work load on the coolant supply valve, which after the initial cool-down is not required to control the coolant at maximum flow and at a high rate of intermittence. On the contrary, at sustained intermittence following near equilibrium the supply valve is only required to control a comparatively small coolant flow at moderate on/off rates. As a result of matching coolant flow to actual requirements, the temperature control system outlined, when compared with the prior art, enables a closer temperature control to be maintained with a lower consumption of coolant and much less hammering of the supply valve. The venting valve is less heavily loaded, of course, because it would serve no purpose if it were to be opened when the supply valve was not open and at all events its on/off rate is always less than that of the supply valve which provides the main control of coolant flow.

The inadequacy of the prior art single-valve control is thrown into particular relief where a chamber of comparatively large volume is to be cooled down rapidly to a temperature of $-100°$ C. and even lower. The oven of a gas chromatograph is a striking example of such chamber, not only because of its volume and the low temperatures to which the chromatographic column within it must be exposed at times as part of the chromatographic process but also because the situation is further aggravated by the fact that a substantial part of the sample injector is made to protrude into the oven in order to minimize the formation of "cold spots". Furthermore, the injector is actually heated. Similarly for the detector, to which the output end of the column is connected. The protruding parts of the heated injector and the heated detector represent a thermal capacity and a source of heat that together with the thermal capacity of such parts as the column and other fittings within the oven make up an aggregate thermal load that must be accounted for in terms of coolant flow.

It is to be understood that, although the term "oven" is normally associated with the provision of temperatures well above ambient, it is proper to refer to the chamber within which the chromatographic column is located by that term even when for analytical purposes the chamber may be cooled down to low sub-zero temperatures. This convention is well understood in the chromatographic art.

It will now be appreciated that when a chromatographic oven is to be cooled down to say $-100°$ C. at a comparatively high rate, compatible with an analytical run of reasonable duration, it is almost inevitable that the flow of coolant required to perform the task will be such as to cause the coolant in the transfer line to be in the liquid state. As long as the single solenoid valve of the prior art remains open to effect rapid cool-down, no particular problem arises.

However, as the temperature drops to the desired lower value and the single solenoid valve enters the intermittent mode of operation referred to earlier, typically controlled by means for adjusting the duration of the open and closed periods of the valve in response to a temperature sensor located in the oven, the coolant reaching the single solenoid valve may unpredictably alternate between the liquid and the vaporized state, around the temperature corresponding to a threshold between the two. It has been realized that the ON period occurring whilst the coolant is in the liquid state is more effective than the same period when the coolant is in the vaporized state. In other words, if the relationship between temperature sensor signal and the on/off operation of the valve is satisfactory for maintaining the temperature of the oven at a given value when the coolant is in the liquid state the same relationship will not be satisfactory when the coolant is in the less effective vaporized state. It follows that, when the temperature has been depressed to a value near that which marks the threshold between the two states, two successive valve openings may encounter the first one state and the second the other state and there will be a tendency for the system to hunt around the threshold and for unpredictable temperature excursions to occur away from the desired lower value.

In a second embodiment of the present invention, particularly suitable for cooling a chamber of comparatively high volume and/or high thermal capacity down to $-100°$ C. and lower by flowing therethrough vaporized liquid gas at a comparatively high flow rate and, therefore, possible risk of the coolant reaching the coolant circuit in the liquid state, there may be provided within the chamber a heat exchanger through which the coolant must pass before reaching the means for automatically selectively supplying coolant to the chamber a-nd the venting orifice.

The heat exchanger may be in the form of a coolant vaporizing duct adapted to be connected to the output end of a transfer line from a Dewar and so constructed and arranged that at a predetermined maximum coolant flow rate any coolant approaching the upstream end of the coolant vaporizing duct in the liquid state will have vaporized by the time the coolant reaches the means for automatically selectively supplying coolant to the chamber and the venting orifice, the vaporizing heat having been supplied by the chamber.

The coolant vaporizing duct may be given any appropriate configuration to maximize heat transfer between the chamber and the coolant, even though a pipe of suitable length and bore may be adequate in certain applications. It should be noted that the heat transfer actually assists the cooling of the chamber and therefore tends to reduce coolant consumption.

As a further contribution to reducing coolant consumption, means may be provided for setting up the venting orifice within the chamber.

Features referred to in the first embodiment may be selectively included in the second embodiment. The advantages over the prior art realized in the first embodiment in terms of lower coolant consumption, closer temperature control and very much reduced valve hammering are reflected in the second embodiment.

The present invention in part springs from the realization that wherever the desired lower temperature permits it closer temperature control of the chamber after the initial cool-down can be achieved by flowing the coolant therethrough in the vaporized state. However, it has also been realized that if the desired lower temperature is such that it can only be reached by flowing liquid gas in the liquid state, steps must be taken to ensure that the coolant is prevented from vaporizing in any part of the coolant circuit, thus avoiding some of the drawbacks of the prior art dwelled upon earlier. This means that fresh coolant in the liquid state must continuously replace the coolant in the transfer line and the coolant circuit which has suffered heat transfer from ambient, in order to prevent a temperature rise in both and possible formation of vaporized coolant. Note that when the coolant flow to the chamber is interrupted for temperature control purposes the coolant warms up if no by-pass flow is provided.

In a third embodiment of the present invention, particularly suitable for cooling a chamber down to temperatures that can only be attained by flowing liquid gas in the liquid state therethrough, the means for automatically selectively supplying coolant to the chamber and the venting orifice may include a two-way controlled valve for routing liquid coolant from a transfer line either to the chamber or the venting orifice but not both at the same time.

As in the previous embodiments, the controller may include a microcomputer responsive to dedicated software. The microcomputer may be so conditioned by the software that during the initial cool-down the two-way valve is switched to the chamber and, therefore, no coolant is vented through to the venting orifice.

The micro-computer may in addition be so conditioned that following the end of cool-down the desired lower temperature is maintained by intermittently switching the two-way valve between the chamber and the venting orifice so as to supply coolant to the chamber at such frequency as may be required to offset any heat transfer thereto, such as from ambient, tending to warm the chamber above the desired lower temperature.

The vaporization of the coolant may be prevented by ensuring that the cumulative effect of coolant flow through the two-way valve is sufficient to prevent critical warming up of the transfer line and the coolant circuit.

The use of the two-way valve as outlined means that no coolant is vented unnecessarily when minimum flow conditions are maintained through the chamber once temperature equilibrium is closely approximated.

A two-way valve may be readily simulated by joining two identical solenoid valves with their bases in good thermal contact and commoning the two input ports such as by means of a manifold to which the transfer line is also connected.

All in all, the present invention has identified the fundamental problem that has prevented the prior art from providing a liquid-gas temperature control system that is satisfactory in terms of a) closeness of the controlled temperature achieved to the desired lower valve set by the operator, b) economical coolant consumption, c) acceptable valve life and d) tolerable noise, and has provided a simple and expedient solution thereto.

The fundamental problem is that the prior art has attempted to control flow during the temperature stabilization stage at the same maximum rate required for fast cool-down. This is the major reason for the poor results obtained by the prior art in terms of a) to d) as referred to hereabove. The solution provided by the invention is to control both the supply of the coolant to the chamber within which an object is to be brought down to the desired lower temperature and the venting of the coolant through a venting orifice in response to the actual temperature of the chamber compared to the set lower temperature. By introducing controlled venting in relation to controlled supplying of the coolant, the means for automatically selectively supplying coolant to the chamber are all able to operate under vastly reduced loading, which enables great improvements to be realized in terms of a) to d) as aforesaid.

Having identified the major problem besetting the prior art, and provided a general solution, the invention has also identified a subsidiary problem, associated with the changing physical state of the coolant, which has a major bearing on the closeness of temperature control that may be achieved: the widely differing effectiveness of the control action depending on whether the coolant is flowing through in the vaporized state or the liquid state. The solution to the subsidiary problem may be expressed in the context of each of the following three situations:

1. Chamber of low volume and/or thermal capacity and extreme desired lower temperatures close to the liquefying temperature of the coolant not required;
2. Chamber of considerable volume and/or capacity but extreme desired lower temperatures, as aforesaid, not required;
3. Extreme desired lower temperatures required.

In broad conceptual terms, the first situation is expediently met by pre-arranging the temperature control system for use of vaporized liquid gas throughout the entire temperature control operation involving an initial fast cool-down stage and a subsequent temperature stabilization stage at the desired lower value, although, somewhat less expediently, liquid coolant might be used during cool-down if exceptionally fast cool-down rates must be attained; the second, by ensuring that the coolant is prevented from flowing through the coolant circuit in the liquid state, at least during the temperature stabilization stage; and, finally, the third by preventing the formation of vaporized coolant during both the cool-down and the temperature stabilization stage. In more general terms, flow control during the temperature stabilization stage should be applied on the coolant on either the vaporized state or the liquid state but not a combination of the two states. The advantage derived from the solution of the subsidiary problem are additive to those derived from the solution of the fundamental problem.

DETAILED DESCRIPTION OF THE INVENTION

Figure 1:
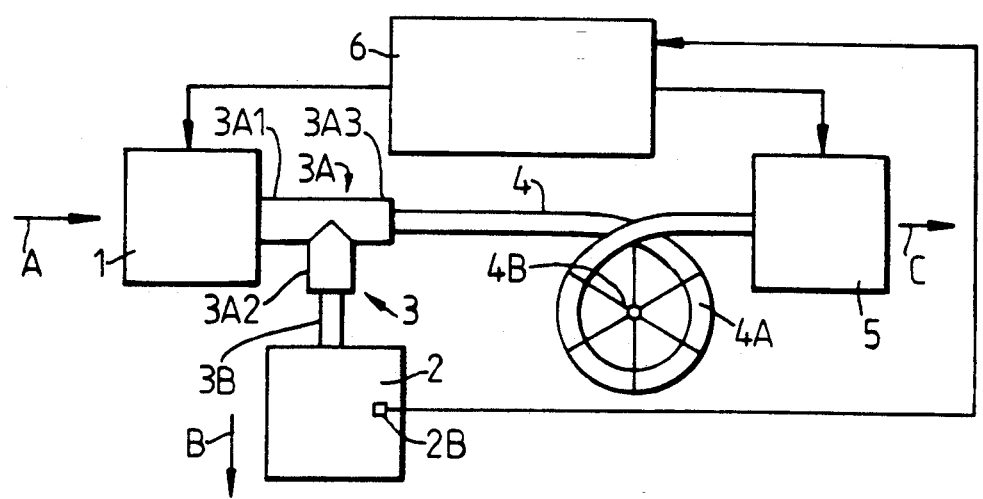
FIG. 1 is an introductory schematic representation of FIG. 2.

In FIG. 1, a temperature control system in accordance with the present invention comprises, in broad diagrammatic outline: an automatically controllable coolant supply valve in the form of solenoid valve 1; a chamber 2 arranged to allow a small leakage of coolant to atmosphere which is either inherent in the design (see FIG. 5) or introduced by means of a vent (see FIGS. 2A and 2C); a coolant supply duct 3 comprising limbs 3A1 and 3A2 of a T-piece connector 3A and a pipe 3B joined to the limb 3A2, the limb 3A1 forming a direct connection with the output port (not shown) of solenoid valve 1 and the pipe 3B feeding into chamber 2; a coolant venting duct comprising limb 3A3 of T-piece 3A joined to a pipe 4, including a coiled portion 4A to be exposed to warming air from a fan 4B, said pipe feeding into the input port (not shown) of a coolant venting valve in the form of solenoid valve 5, the output port of which represents or leads to a venting orifice (see FIG. 2); and a controller of solenoid valves 1 and 5 in the form of a microcomputer controller 6.

Within the chamber 2 is located a temperature sensor 2B, which is provided with a pair of leads (as will be shown later) extending to the controller 6. If the chamber 2 is intended to house essentially a particular object to be cooled, e.g. a cold trap tube, the temperature sensor is advantageously a localized sensing device, preferably a thermocouple in good thermal contact with the object. On the other hand, if the chamber encloses several objects instead, or the temperature of the enclosed space is of dominant importance, e.g. in cooling the oven of a gas chromatograph, the temperature sensor is advantageously a diffuse device, preferably a platinum resistor sensor, located within the chamber but not in contact with any of the objects therein. Reference 2B is therefore identified with a generic sensor where the situation admits of both specific sensors, such as in describing the temperature control system with reference to FIGS. 3 and 4, or is identified with one or other specific sensor where one is preferred to the other, such as in the description of FIGS. 2A, 2B, 2C and 5.

The aforementioned coolant supply valve 1, coolant venting valve 5, coolant supply duct 3, coolant venting duct 4 a-nd chamber 2 will henceforth be regarded as forming cooperating parts of the cooling circuit introduced earlier.

In operation, liquid nitrogen from a nitrogen Dewar (not shown) is fed to the input port (not shown) of valve 1 in the direction of arrow A and, when valve 1 is open, is conveyed through limbs 3A1, 3A2 and pipe 3B to chamber 2, from whence it is allowed to leak to atmosphere in the direction of arrow B through a vent or simultaneously from a number of inherent leakage points, after having diffused throughout the chamber 2.

In addition, coolant is passed to the input port of solenoid valve 5 via limbs 3A1 and 3A3 and pipe 4, with the result that when valve 5 is open some coolant will vent through the output port (not shown) of valve 5 to atmosphere, in the direction of arrow C.

Figure 2:
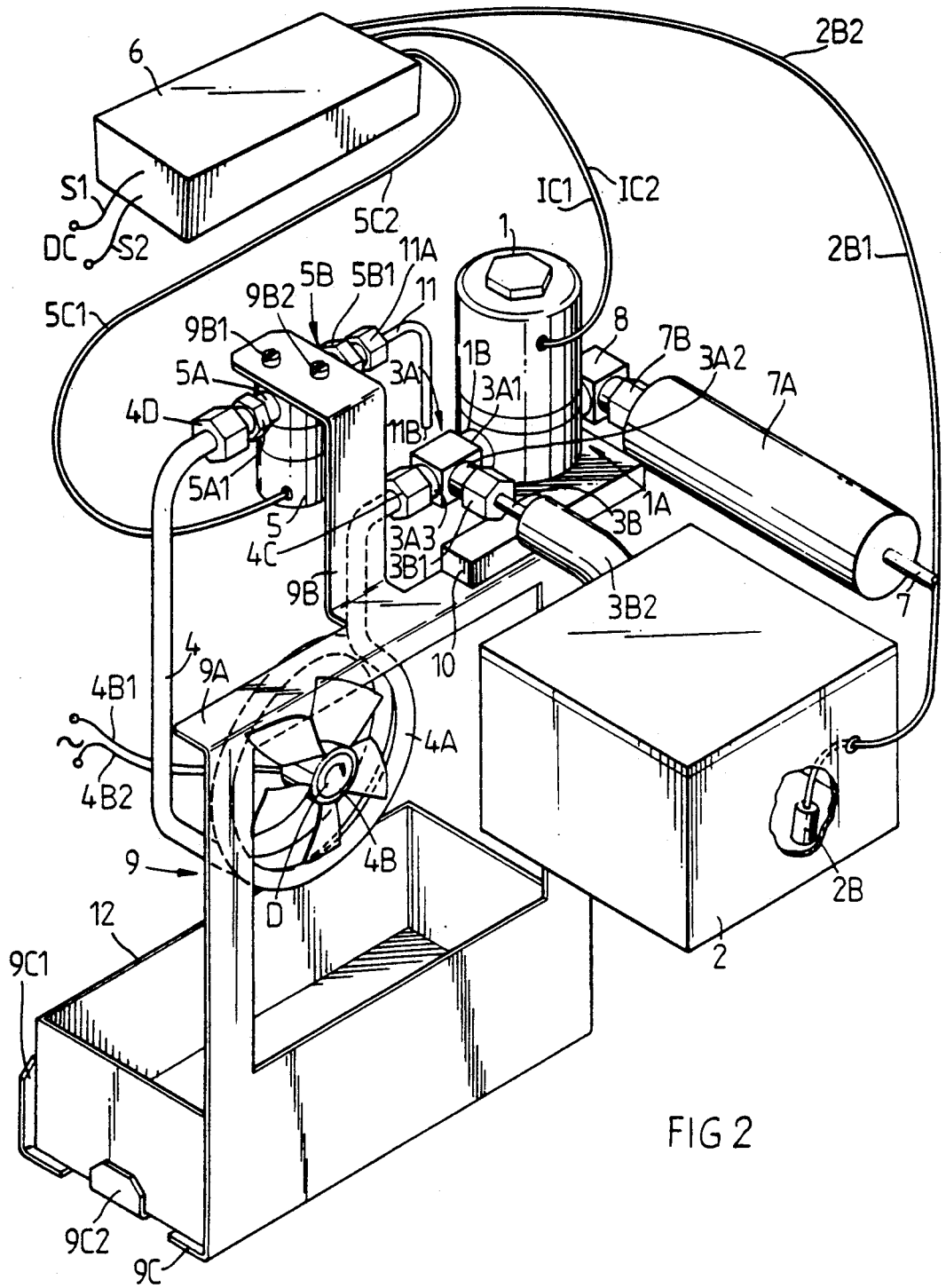
FIG. 2 is a representation of a basic practical embodiment of the invention from which other embodiments are derived.

With reference to the embodiment of FIG. 2, a coolant transfer line 7, provided with a thermally insulating sleeve 7A to minimize heat leakage from ambient when transferring coolant from a nitrogen Dewar, as referred to earlier, is shown connected in gas-tight manner to the input port IA (hidden from view) of solenoid valve I via a right-angle connector 8, one limb of which is screwed into the said port 1A and the other is in screw engagement with the pipe union 7B of transfer line 7. Solenoid valve 1 is supported on a flange 9A of a frame 9 via a thermally insulating slab 10 retained by screws applied from the underneath of the flange 9A and, therefore, not seen in FIG. 2.

To avoid unnecessary repetition, all connections within the coolant circuit shown in FIG. 2 will henceforth be understood to be gas-tight threaded connections involving male and female pairs.

The output port 1B of solenoid valve 1 is connected to the limb 3A1 of T-piece 3A and the coolant supply duct 3 (FIG. 1) is completed through the connection of pipe 3B to the limb 3A2 via a pipe union 3B1. Pipe 3B is thermally insulated by resilient sleeve 3B2, which penetrates the chamber 2 and forms a seal therewith at the point of entry.

Limb 3A3 of T-piece 3A is connected to pipe 4, including coiled middle portion 4A, by means of a pipe union 4C. A similar connection is established at the downstream end of pipe 4, involving engagement between a pipe union 4D and an adapter 5A1, screwed into the input port 5A of solenoid valve 5, the latter being supported on a bracket 9B, integral with frame 9, by means of screws 9B1 and 9B2. Adaptor 5B1 and pipe union 11A cooperate in like manner to make a connection between venting pipe 11 and the output port 5B (hidden from view) of valve 5. The end 11B of pipe 11 represents the venting orifice. If the pipe 11 is omitted, the output port 5B acts as the venting orifice.

In addition to supporting the solenoid valves 1 and 5, the frame 9 retains a drip tray 12 by a lower angled extension 9C provided with upturned retaining flanges such as 9C1 and 9C2. The dip tray 12 is preferably a plastics tray and serves the purpose of collecting drips, from the coolant circuit above it, resulting from the surface frost formation due to ambient humidity, when the circuit is operative, and the subsequent defrosting, when it is turned off.

The main operational requirement of valve 1 is that it be capable of performing satisfactorily at temperatures well below $-100°$ C. The same requirement has been circumvented in the case of valve 5 by providing the coiled portion 4A in pipe 4 and causing warming air from fan 4B to impinge on the said portion.

Fan 4B as depicted in FIG. 2 is a well-known readily available 5-bladed fan with in-built electric motor. The hub of the fan is integral with the rotating part of the motor marked by a circular arrow D denoting the direction of rotation. The stationary part faces the coiled portion 4A and it is not seen; it is linked to a supporting frame by struts. The struts and the frame have been omitted because they would have largely obscured the view of the coiled portion 4A. The motor is energized from an alternating power supply, such as the public supply, marked by the symbol shown, via leads 4B1 and 4B2.

If the temperature control system is part of an apparatus in which heat is generated and an extractor fan is already provided, it is simply a matter of arranging the coiled portion to be located in the exhaust stream of the fan. In FIG. 2 it is assumed that the fan is already available to extract heat from the apparatus of which the temperature control system is a part. If that is not the case, and for any design reason it would be inconvenient to provide a warming fan, the obvious alternative is to omit the coiled portion 4A in pipe 4 and fit a valve 5 which meets the same specification as that of valve 1.

The chamber 2 may assume any required shape and proportions, depending on its purpose and the configuration of the object or objects to be cooled within it. The parallelepipedal aluminium box depicted in FIG. 2 is purely symbolical, therefore, of any convenient shape and size.

As to the electrical layout, the solenoid within valve 1 and that within valve 5 (neither solenoid is visible, of course) are connected to the controller 6 via respective lead pairs 1C1-1C2 and 5C1-5C2. Another pair of leads, 2B1-2B2, connect the temperature sensor 2B to the controller 6 which is energized from a 24-Volt direct current power supply marked DC, via leads S1 and S2.

In FIG. 2, as already stated with reference to FIG. 1, chamber 2 may house a single object the temperature of which is to be closely controlled, in which case the temperature sensor 2B is preferably a thermo-couple welded to the object; or it may house several objects and the temperature of the enclosed space is to be sensed for practical reasons, in which case the temperature sensor is preferably a coiled resistance comprising many turns of very fine platinum wire.

Because the nature of the temperature sensor does not significantly affect the operation of the controller 6, said operation will now be described on the basis that the temperature sensor may be of either kind.

Figure 3:
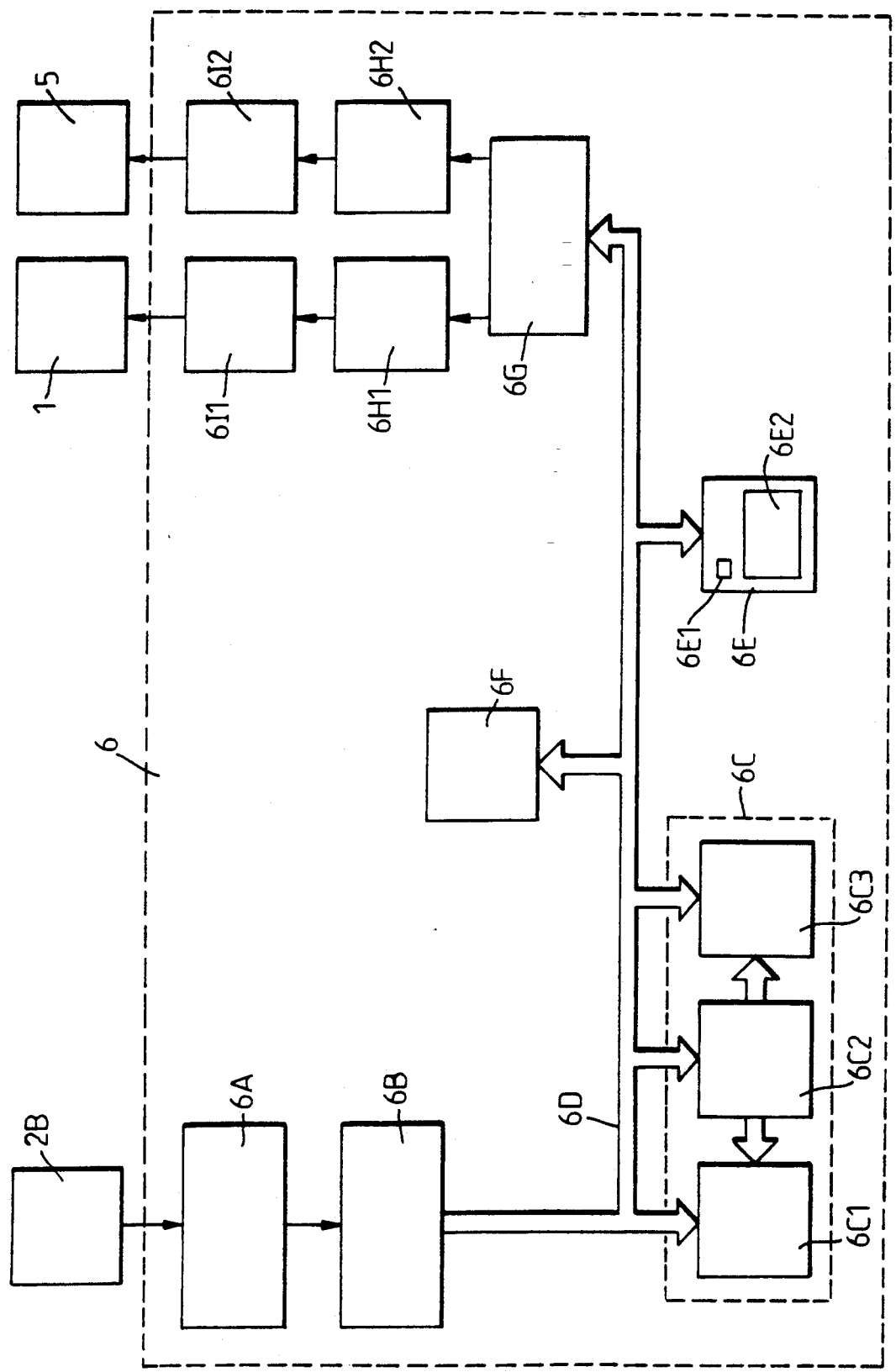
FIG. 3 is a schematic representation of a controller including a microcomputer through which the attainment and stabilization of the desired lower temperature is controlled in each of the embodiments hereof.
Figure 4:
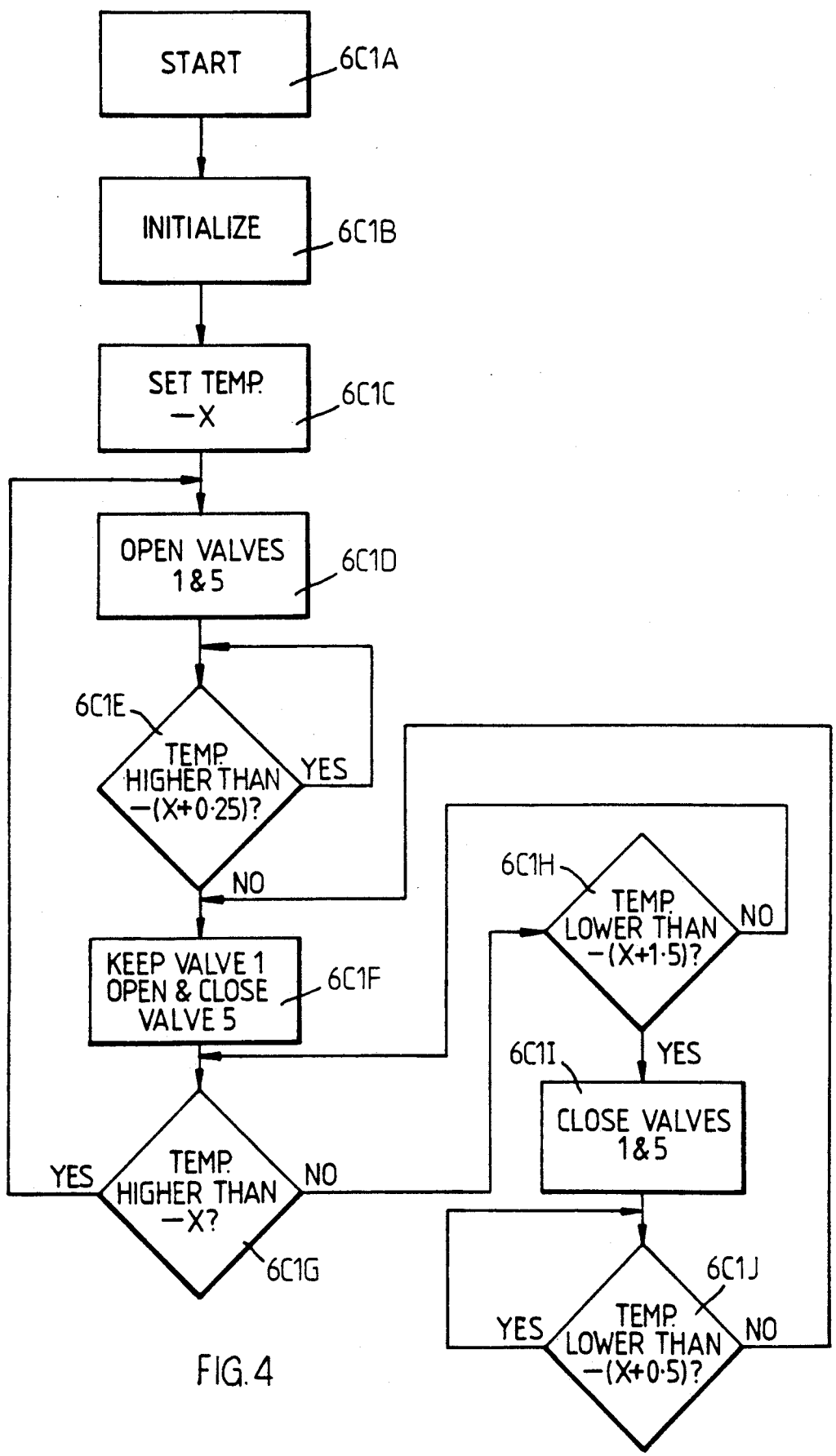
FIG. 4 is a flow chart of the temperature control operations performed by the microcomputer in response to dedicated software in each of the embodiments hereof with the exception of those described with reference to FIG. 6 and 7.
Figure 6:
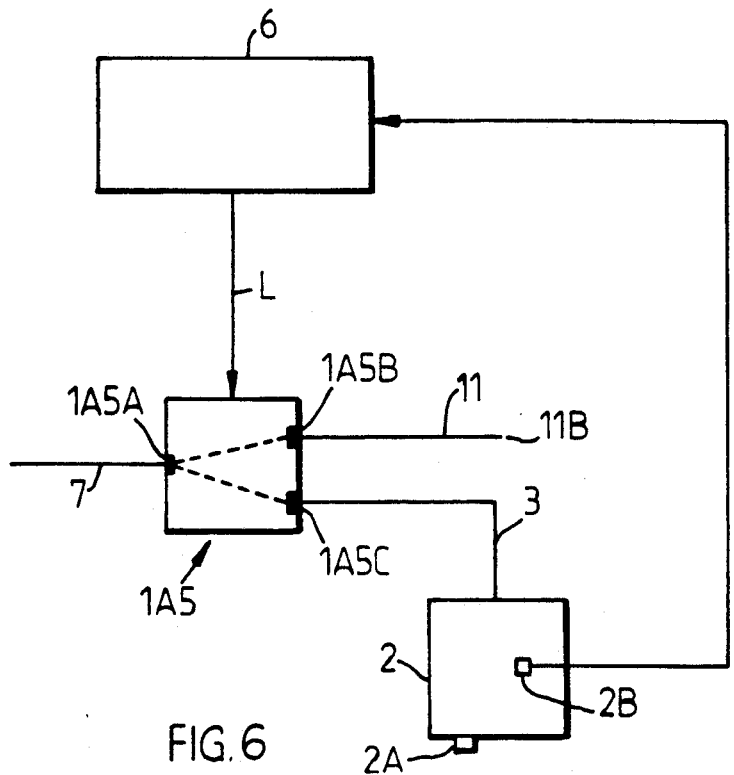
FIG. 6 depicts a modification of the FIG. 2 embodiment enabling extreme desired lower temperatures to be attained and maintained by flowing liquid gas exclusively in the liquid state via a two-way valve.
Figure 7:
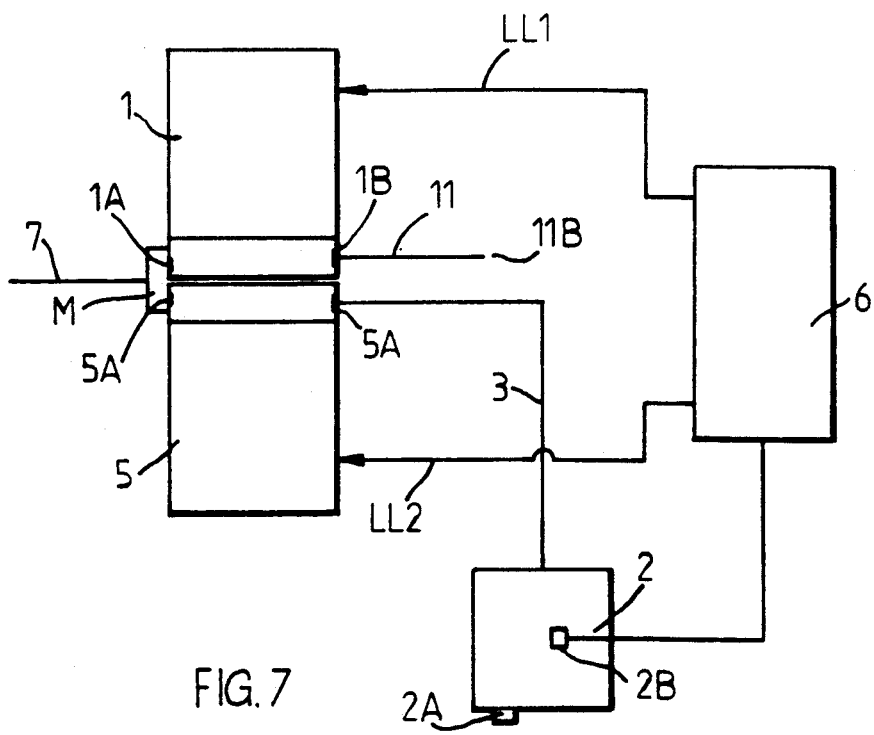
FIG. 7 depicts the FIG. 6 modification with the two-way valve simulated by two identical solenoid valves joined base to base and the two input ports commoned by a manifold.
Figure 8:
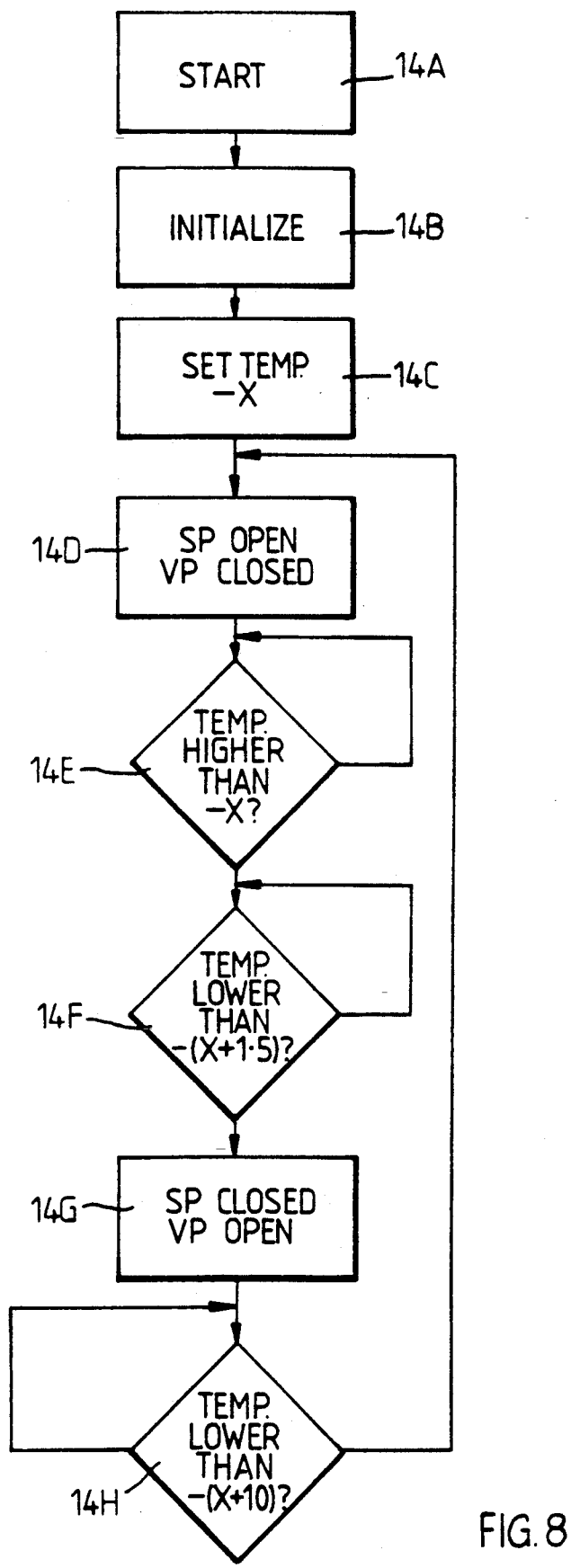
FIG. 8 is a flow chart of the operations performed by the microcomputer within the controller in response to dedicated software applicable to the modifications of FIGS. 6 and 7.

The description of FIGS. 3 and 4 that follows applies to the embodiments of FIG. 2 and derivations therefrom, except that the embodiments of FIGS. 6 and 7 require a software modification in accordance with the flow chart of FIG. 8.

In FIG. 3, the controller 6, represented by the parts within the outer dotted frame, receives an input from the temperature sensor 2B (FIG. 2) and causes energizing outputs to the solenoids within solenoid valves 1 and 5, respectively, to be delivered or interrupted, depending on whether the valves are to be opened or closed. The output of the temperature sensor 2B is amplified by amplifier 6A, changed to digital form by the analogue-to-digital converter 6B, and extended to the microcomputer 6C via a bus 6D communicating with a read-only-memory (ROM) 6C1, a microprocessor 6C2, and a read-and-write memory (RAM) 6C3. The bus 6D also communicates with a keypad 6E, enabling the user to set the desired lower temperature, and a display 6F which shows both the temperature demanded and that actually achieved by the temperature control system. The computed output as determined by a software program stored in the ROM 6C1 is extended to the latch 6G which branches into two channels, one for controlling the valve 1 and the other for controlling the valve 5. The first named channel comprises a driver 6H1 providing sufficient power to operate a relay 6I1, which, in turn, operates the solenoid in valve 1. The second channel comprises likewise driver 6H2 and relay 6I2 operating the solenoid in valve 5.

The period during which each of valves 1 and 5 is open or closed is determined by the software program stored in the ROM 6CI, which compares to the signal from the temperature sensor 2B with the desired lower temperature set on the keypad 6E and conditions the microcomputer 6C to operate the latch 6G and control the solenoid in valve 1 via driver 6H1 and relay 6I1 and the solenoid in valve 5 via driver 6H2 and relay 6I2 to establish the coolant flow conditions that will cool the chamber 2 to the set temperature. It is, of course, well known that conventional solenoid valves admit of only two states: fully open, when energized, and fully closed, when deenergized, although the inverse status may be arranged if required.

The program stored in the ROM 6C1 actually implements the requirements set out in the flow chart of FIG. 4, which shall now be described in detail.

In FIG. 4, the following description of which includes references found in the applicable of FIGS. 1 to 3 (quod vide), the sequence of operations commanded by the software actually commences at 6C1B, when the microcomputer performs the initialization procedure such as setting the RAM memory 6C3 to zero, the preceding block 6C1A merely pointing to the initial intervention by the operator in the act of switching on the controller by pressing a toggle key 6E1 on the keypad 6E. After initialization has taken place, the operator is prompted via the display 6F, to enter the desired lower temperature by pressing the appropriate keys in a calculator-type key matrix 6E2 of keypad 6E. This is indicated at 6C1C and marks the second and final intervention by the operator in any one run. Note that the X preceded by the minus sign stands for any desired lower temperature as set on the keypad 6E. The minus sign signifies a value lower than a higher actual temperature. It does not necessarily denote a sub-zero temperature.

The first valve control operation commanded by the program occurs in the manner specified at 6C1D, whereby both solenoid valves 1 and 5 are fully opened to enable a rapid cool-down of the chamber 2 and its contents from ambient temperature to the set desired lower temperature. While the cooldown is in progress, the temperature within the chamber 2 is sensed by the temperature sensor 2B and, under software control, is compared with the set value stored in the RAM 6C3 to establish first whether, in accordance with 6C1E, the actual temperature within the chamber 2 is higher than the desired lower temperature (represented by $-X$) lowered by 0.25° C., e.g. assuming the set temperature to be $-100$, is the actual temperature higher, i.e. warmer, than $-100.25$? If the answer to the question is "Yes", the software enters into a waiting loop, as indicated by the YES branch in 6C1E. If it is "No", the NO route to 6C1F is followed and, consequently, the software will command that valve 1 be kept open and valve 5 be closed. This means that the cooling effect is being reduced, although the flow of coolant through the chamber 2 is being maintained and it is in fact slightly increased, but at a higher temperature since valve 5 is not assisting in maintaining a high total flow made up of chamber flow and venting flow and as a result the coolant conveying parts affected by ambient temperature will start to warm up slightly.

Monitoring of the actual temperature by the software is continued in order that the question asked at 6C1G be answered. The question suggests that the requirement of the control system is for the actual temperature not to rise significantly above the set point, and we shall presently observe that excursions below the set point are permitted within comparatively narrow limits. Now, if the answer is "Yes", more cooling is required and the YES route is seen to branch back to 6C1D, with the result that the sequence described from that point is repeated. Branching back in the software persists until the answer becomes "No", in which case an answer is due to the question asked at 6C1H: whether the actual temperature has fallen 1.5° C. below the set point. If it has not, the NO branch indicates that the software will enter into a waiting loop. If the answer is "Yes", it means that the actual temperature has fallen beyond the predetermined limit and that therefore less cooling must be applied. Consequently, it is requested at 6C1I that both valve 1 and valve 2 be closed. The effect of this last operation must be monitored and the question asked at 6C1J answered by the software. If the temperature is not more than 0.5° C. lower than the set point, all is well and the software may be put into a waiting loop, otherwise the NO route must be followed to 6C1F and the sequence repeated from there. Several iterations may be required before the system settles down to a comparatively steady state. When this is closely approximated, the actual temperature will largely remain below the set point, which means that the answer to 6C1G will tend to be "No" and that control largely involves the steps denoted by 6C1H, 6C1I and 6C1J, when valve 1 is intermittently opened and closed and valve 5 tends to be mostly closed, unless an occasional disturbance causes the actual temperature to rise, in which case the system reacts by opening valve 5 momentarily through the loop including 6C1D until the disturbance has been overcome and the loop including 6C1F becomes operative again.

The embodiment so far described with reference to FIG. 2, FIG. 3 and FIG. 4 may be adapted for specific applications, some of which will determine the shape, size and other physical characteristics of the chamber 2. In some applications, no vent is required to allow the coolant to flow through because the enclosure acting as a chamber is almost inevitably leaky, e.g. the oven of a gas chromatograph. In others, a vent with or without a non-return valve is desirable, e.g. in the housing of a cold trap. The chamber 2 in FIG. 2 is symbolical of both situations, as will be presently appreciated.

Typically, chamber 2 may house a cold trap comprising in essence a cylindrical tube containing an adsorbent in which a gaseous analytical sample is trapped whilst the temperature of the tube is maintained at a desired lower value over an extended period, followed by a very short interval during which the temperature is raised to a comparatively high value to effect thermal desorption of the sample in the form of a "plug" concentrated in time, typically for injection into the column of a gas chromatograph.

Such a cold trap is described in UK Patent No. 2 085 309, which is imported in full into the present application. In FIG. 3 of the said patent the cylindrical tube is represented by the U-tube 1, which is adapted for ohmic heating, cooperates with the thermo-electric pump 7 and is contained within a housing 9 that is readily adapted in accordance with the present description to act as a chamber 2 (FIG. 2) to depress the U-tube 1 well below the sub-zero temperature attainable with the thermo-electric pump 7. In essence the chamber 2 as shown in FIG. 2 hereof may replace the housing 9 in FIG. 3 of the imported patent with the addition of a vent which is in essence a suitably sized orifice in a wall of chamber 2 or the vent 2A referred to in the description of FIG. 2A. The temperature control system of the present invention is simply superimposed on that of the imported patent whenever the lower sub-zero temperatures are required without any need for isolating the thermo-electric pump. Although the thermo-couples 1B1 and 132 (FIG. 3 of imported patent) could be shared by controller 6 of FIG. 3 and 4 hereof, a further thermo-couple also welded to the U-tube 1 is preferred to facilitate superimposition of the system in accordance with the present invention without interfering with the existing temperature control provided in the imported patent.

Figure 2A:
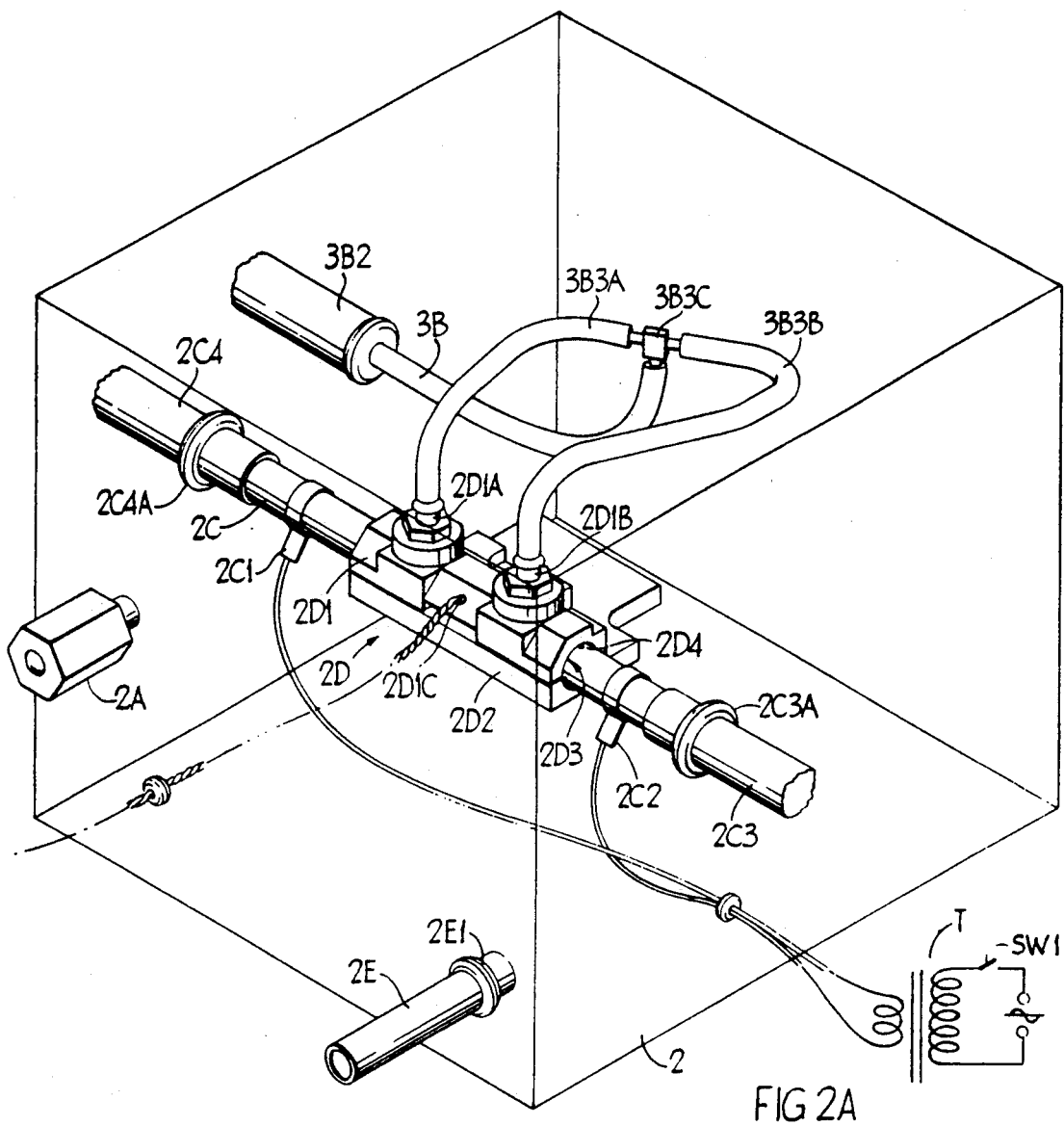
FIG. 2A depicts a derived embodiment in an application of the invention to the cooling of a cold trap.
Figure 2B:
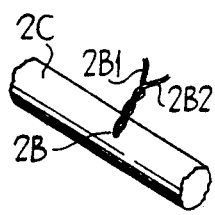
FIG. 2B depicts a detail of FIG. 2A.

The present invention is well suited to meeting the requirements of cold trap applications even more demanding than the one just referred to. Where the thermal capacity of the trap tube must be reduced to a minimum and any extra thermal capacity such as of heat exchangers and the like that might be required for the purpose of liquid gas cooling could not be tolerated, since it would lengthen the heating cycle and therefore extend the period over which the "plug" was formed, thus spreading the length of the plug within the column and spoiling the resolution of the chromatogram, the arrangement of FIG. 2A is particularly advantageous. In FIG. 2A the chamber 2 of FIG. 2 is shown ghosted. It functions as an ante-chamber within which is located the chamber proper as defined within a longitudinally extending jacket 2D made in two halves, 2D1 and 2D2, abutting along an axial plane. The jacket 2D surrounds a straight, cylindrical, thin-walled, stainless steel tube 2C of very low thermal capacity and between the inner wall of the jacket 2D and the outer surface of the tube 2C extends an annular chamber 2D3 the width of which is determined by three projections 2D4 acting as spacers of tube 2C from the inner cylindrical surface of the jacket 2D.

The upper half 2D1 of jacket 2D is provided with two nipples, 2D1A and 2D1B, to which branches 3B3A and 3B3B of pipe 3B are respectively connected by T-piece 3B3C. The said nipples allow the coolant to reach the chamber 2D3, swirl around the tube 2C and escape into the ante-chamber 2 through both longitudinal ends of the chamber 2D3, which ends are left open except for the small obstruction caused by the projections 2D4. They are longitudinally spaced to provide a better distribution of the coolant around the central region of the tube 2C, where the adsorbent is located. The ante-chamber 2 is protected against ingress of ambient moisture both by sealing its lid and pumping dry nitrogen into it via a through pipe 2E cooperating with a grommet 2E1 to guard against small leaks from ambient by maintaining a positive gas pressure within the ante-chamber even when the coolant supply valve 1 is closed. The ante-chamber is provided with a vent 2A fitted with a non-return valve which opens when the pressure within the chamber reaches 0.5 p.s.i. (pounds per square inch). Any moisture trapped within the ante-chamber would have a deleterious effect on the performance of the cold trap since it would amount to a large added thermal capacity that could not be tolerated where it was a design requirement that the overall thermal capacity had to be reduced to a minimum. The jacket 2D is itself of low thermal capacity and the total thermal capacity involved has in fact been reduced to the point where it has a minor effect on the rate at which the temperature of the effective portion of the tube 2C may be raised for the purpose of effecting thermal desorption. Tube 2C contains a suitable adsorbent (not shown) and is provided with two welded leads 2C1 and 2C2 by which the central tube region may be raised rapidly to an elevated temperature by the ohmic heating resulting from passing a heavy current therethrough, via the said leads, from an AC (alternate current) source of supply via step-down transformer T, the primary of which is energized through a switch SW1. The temperature sensor 2B (FIG. 2B), in the form of a thermo-couple, is actually welded to the tube 2C close to its central region, the thermo-couple leads 2B1 and 2B2 passing through an aperture 2D1C in the jacket half 2D1 and extending to the controller 6 (FIG. 2). A gas sample may be conveyed to the tube 2C through a pipe 2C3 and after thermal desorption may be transferred to the chromatographic column of a gas chromatograph (not shown) via pipe 2C4. The ante-chamber 2 is fitted with sealing grommets 2C3A and 2C4A where pipes 2C3 and 2C4 are fed through.

In the embodiment of FIG. 2A derived from that of FIG. 2, the lowest temperature that may be selected is $-100°$ C. The volume of the chamber 2D3 is 1 cc. The combined thermal capacity of the tube 2C and the jacket 2D is indicated by the fact that the cool-down time from ambient to $-100°$ is only 90 seconds and the coolant flow required to achieve it is quite moderate. The impedances to flow of the various constituents of the cooling circuit have been so chosen that at the maximum value of coolant flow required to achieve the desired cool-down time no liquid nitrogen can ever reach the input port of valve 1 and that of course means that all other parts of the cooling circuit downstream of valve 1 must be free of liquid nitrogen, which once vaporized cannot be re-liquefied without subjecting it to very high pressure in a proper liquefying plant. Naturally the impedance of the supply duct feeding into chamber 2D3 and that of the venting duct leading to atmosphere via the venting valve 5 are so chosen one in relation to the other that the combined flow vented to atmosphere through the venting valve 5 and the chamber vent 2A is the smallest that will secure the desired temperature control in accordance with the invention, in order to derive full benefit from the advantage of low coolant consumption. The embodiment of FIGS. 2-2A is particularly apt where cold trap requirements are such that for the most part they can only be met by liquid gas cooling.

Figure 2C:
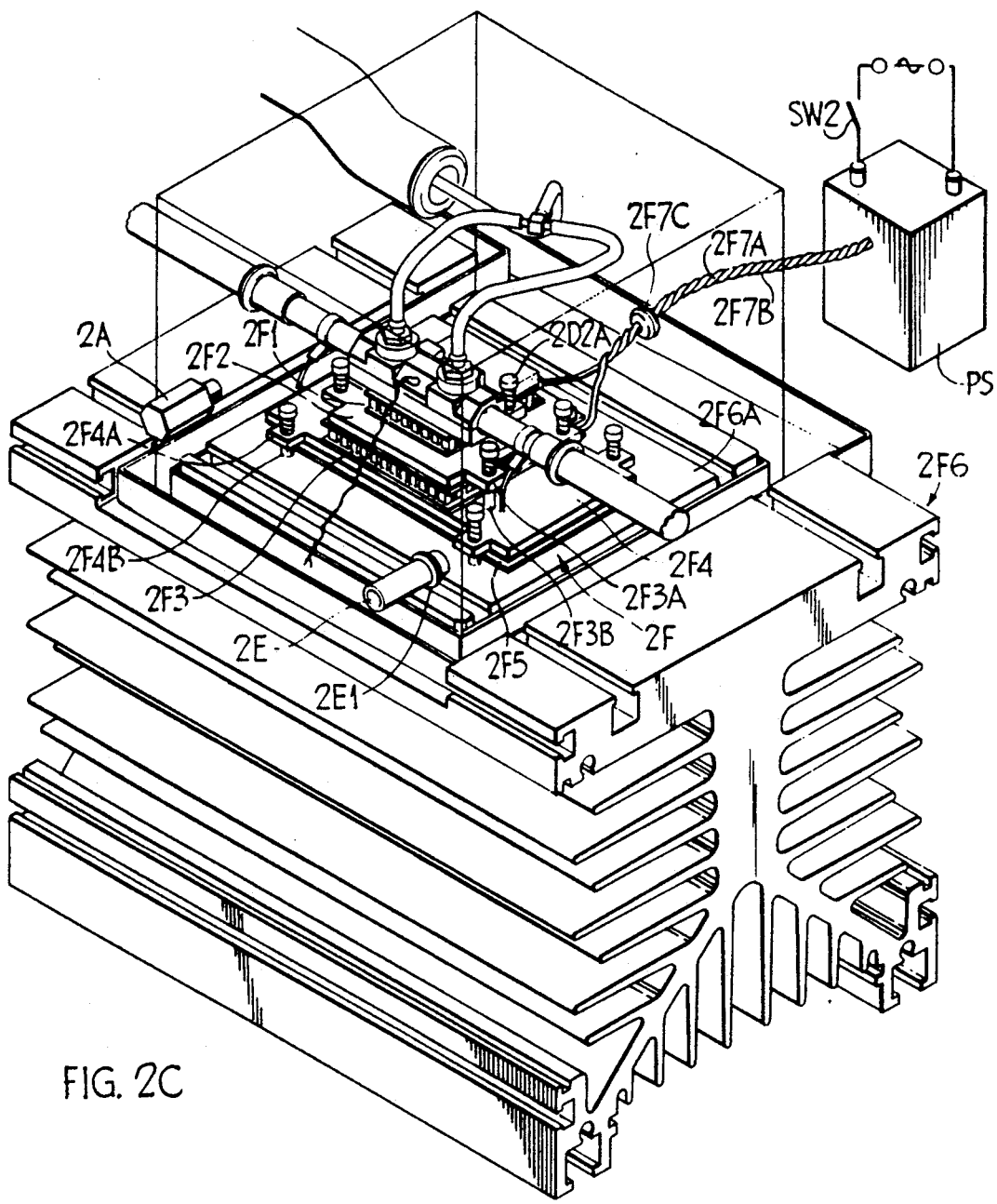
FIG. 2C depicts a derived embodiment in which the cold trap of FIG. 2A is superimposed on a thermo-electric pump.

In FIG. 2C, the jacket 2D as depicted in FIG. 2A has been fitted within the chamber 2 of FIG. 2, which chamber is now acting as an ante-chamber and is shown ghosted. To reduce congestion the referencing of parts in FIG. 2A will not be repeated in the like parts of FIG. 2C, with the exception of reference 2A. To the sane end, the electrical connection between the trap tube 2C and the transformer T will not be shown.

The jacket 2D is shown mounted on the top stage 2F1 of a multi-stage, series-connected, thermo-electric pump 2F having leads 2F7A and 2F7B passing through grommet 2F7C and extending to stabilized DC power supply PS fed from an AC public supply through a switch SW2. Stage 2F1 is in turn supported by an aluminium slab 2F2, which bears on stage 2F3, in turn supported by slab 2F4. The third stage 2F5 is not seen. It lies between the slab 2F4 and the flat top 2F6A of a heat sink block 2F6 which top acts as the floor of the ante-chamber 2, shaped in the form of a hood the base rim of which rests on the heat sink 2F6 and is sealed thereto. The ante-chamber 2 is fitted with a vent 2A as in the case of the ante-chamber 2 in FIG. 2A.

All pairs of contacting surfaces are bonded together in such manner as to reduce as far as possible the thermal impedance therebetween. Slab 2F4 is provided with four lugs 2F4A for securing the entire stack to the top 2F6A of the heat sink 2F6 by means of nylon screws 2F4B. Similarly, slab 2F2 is secured to slab 2F4 by cooperating lugs 2F3A and nylon screws 2F3B. Finally, the jacket half 2D2 (FIG. 2A) is secured to the slab 2F3 by nylon screws 2D2A.

The operation of the thermo-electric pump 2F in cooperation with the heat sink 2F6 is well known and is touched upon in the imported patent. It is independent of the operation of the liquid gas temperature control system and gives the user the option of attaining the desired lower temperature either by means of the thermo-electric pump or the liquid gas system down to say −50° C. or overriding the thermoelectric pump down to −100° C. Clearly, the embodiment of FIGS. 2-2C fits a situation where a thermo-electric pump will normally serve, but often the cooling demands can only be met by using liquid gas as a coolant. The temperature control system in accordance with the invention may advantageously form part of an accessory to a thermoelectric pump system.

Note that even when the thermo-electric pump 2F is being overridden some heat will still be dissipated via the heat sink 2F6. This heat is utilized by the fan 4B (FIG. 2) for drawing air through the fins of the heat, sink and exhausting it onto the coils 4A.

It will now be appreciated, of course, that FIG. 2 refers to an embodiment in which the arrangement within chamber 2 is generalized so that, by specifying different arrangements, embodiments may be derived all of which share in all other respects the construction and operation as described with reference to FIG. 2. Thus FIG. 2 in conjunction with FIG. 3 of the imported patent refers to a first derived embodiment in which a temperature control system in accordance with the present invention may be superimposed on the cold trap described in the said patent, so that either system may be used independently of the other or with the present system overriding the old system. Likewise, FIG. 2 in conjunction with FIGS. 2A and 2B refer to a second derived embodiment wherein the chamber 2 functions as an ante-chamber to a chamber proper within it, which has very low volume and thermal capacity and forms part of a cold trap with a particularly fast thermal response. Finally, FIG. 2 and FIG. 2C relate to a third derived embodiment wherein liquid cooling in accordance with the second derived embodiment is superimposed on thermo-electric cooling as in the first derived embodiment.

Figure 5:
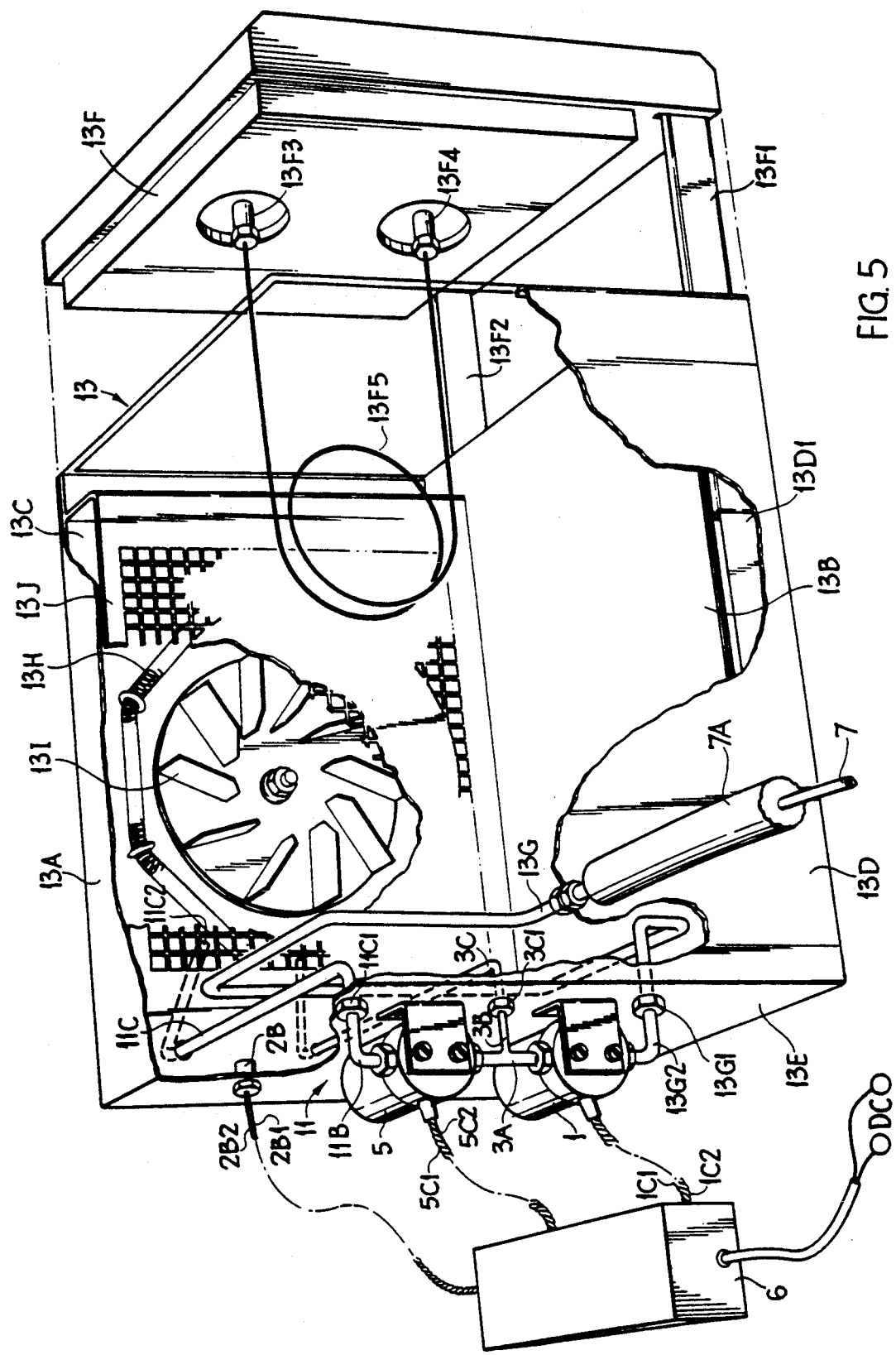
FIG. 5 is a representation of a derived embodiment in an application of the invention to a chromatographic oven.

In FIG. 5 the two-valve temperature control system as depicted in FIG. 2 has been slightly modified to make it suitable for operation in a situation where the chamber is of considerable volume and thermal capacity and, therefore, the possibility of the coolant reaching the supply valve 1 (FIG. 2) in the liquid state cannot be ruled out, as observed earlier. In FIG. 5, the symbolical chamber 2 in FIG. 2 takes the form of a chromatographic oven 13 as part of a gas chromatograph (not shown). The oven proper is a space of typically 10,000 cc capacity within a parallelepipedal box formed by five fixed walls: a top wall 13A, a bottom wall 13B, two side walls 13C and 13D, a rear wall 13E and a front wall 13F having runners 13F1 and 13F2 slidable, respectively, on rail 13D1 fixed to wall 13D and rail 13C1 (not seen) fixed to wall 13C. The wall 13F is in effect a slidable door which when open allows access to the interior of the box, i.e. the oven 13, and when closed completes the oven 13 as a chamber thermally insulated from ambient to some extent, but inevitably permitting some heat transfer to take place in the form of leakage.

Gas chromatographic ovens are not normally hermetically sealed from ambient when the door is closed. In fact, the air leakage is such that no provision need be made for venting the coolant when liquid gas is used. Oven 13 is no exception and a structurally defined vent such as depicted in FIG. 2A is not required.

Fixed to the door 13F is a chromatographic injector 13F3 and a chromatographic detector 13F4, the input end of a chromatographic column 13F5 being connected to the first and the output end to the second. It will be noted that the injector 13F3 and the detector 13F4 actually protrude into the oven space when the door 13F is closed.

FIG. 2 and FIG. 5 share a number of common parts. Like parts have therefore been given like references. The control of the supply valve 1, through leads 1C1, 1C2 and the venting valve 5, through leads 5C1, 5C2, by the controller 6 is as described with reference to FIGS. 2, 3 and 4.

As to the coolant circuit, one important modification is in that the transfer line from the Dewar is not connected to the coolant supply valve 1, direct. In fact the transfer line 7 is joined in operation to an internal coolant vaporizing duct 13G, which runs close to the rear of wall 3E and forms an almost complete loop following roughly the contour of said wall before ending in a pipe union 13G1 external of wall 13E by which it is connected to the input port of valve 1 via a short piece of angled pipe 13G2. To the output port of valve 1 is connected one end of the vertical limb (as drawn) of a fabricated T-pipe 3A (the T-piece connector and adaptor of FIG. 2 have been dispensed with to simplify the drawing in a congested area, although the reference 3A has been retained) the other end being connected to the coolant venting valve 5, which performs the sane function as valve 5 in FIG. 2 but is in fact physically identical with valve 1 in both FIG. 2 and FIG. 5. The arrangement of FIG. 2 involving a venting valve of lower specification made possible by the action of the warming loop 4A has been omitted since at the high rate of coolant flow required in the chromatographic application it is more important to lower coolant consumption than to reduce the cost of the venting valve. The horizontal (as drawn) limb 3B of T-pipe 3A is prolongated via external pipe union 3C1 into an extension pipe 3C within the oven 13. The coolant supply duct comprising parts 3A1, 3A2 and 3B in FIG. 1 is defined by the lower half of the vertical limb of T-pipe 3A, the horizontal limb 3B, the union 3C1 and the extension pipe 3C in FIG. 5. The coolant venting duct comprising parts 3A1, 3A3 and 4 in FIG. 1 is represented by the two vertical limbs of the T-pipe in FIG. 5.

A venting pipe 11 is connected to the output port of valve 5. It has been simplified compared with its counterpart in FIG. 2 and is seen to comprise an angled pipe 11B joined by external pipe union 11C1 to extension pipe 11C running for a predetermined length within oven 13, the end 11C2 of pipe 11C representing the venting orifice.

It will be noted therefore that in the interest of lowering coolant consumption both the coolant supply duct and the coolant venting duct are led within the oven 13 at a short distance from the valves supplying them.

Within the oven 13, adjacent wall 13C, is located a heater coil 13H and an electric fan 13I, both behind a grid 13J, the combined thermal capacity of which is quite significant and adds to the total thermal capacity of the oven that must be accounted for in the cooling process. Equally important is the fact that both the injector 13F3 and the detector 13F4 attached to the oven door 13F not only represent still further thermal capacity that cannot be ignored but, worse still, such devices are normally heated to prevent cold "spots" forming between each end the chromatographic column 13F5 and the device to which the end is joined, as shown. A temperature sensor 2B, in the form of a coiled platinum resistance to which the temperature control system as described with reference to FIGS. 2, 3 and 4 responds, is also located within the oven adjacent wall 13C, in an advantageously chosen location for sensing the space temperature of the oven 13. It is provided with leads 2B1 and 2B2 by which it is connected to controller 6.

Clearly the total thermal capacity to be accounted for in a chromatographic oven is quite considerable, which means that when the desired lower temperature is particularly low or the expected cool-down rate particularly rapid, or both simultaneously, the coolant flow required is so high that, as a result, the coolant could well be in the liquid state up to any point in its progress through the coolant circuit as a result. For reasons that have been given earlier, this leads to an unsatisfactory situation, with poor temperature control and high coolant consumption, if a single control valve is used in accordance with the prior art. The two-valve control as described with reference to FIG. 2 would constitute an improvement even in such extreme situation, in that maximum coolant flow is only maintained during the cool-down stage, when both valves 1 and 5 are open. Thereafter, valve 5 is mostly closed, which means that valve 1 is actually operative on a reduced flow and that at such flow the coolant reaching valve 1 from the transfer line 7 is likely to be in the vaporized state due to the longer exposure to ambient heat of the slowly flowing coolant. However, by feeding valve 1 not directly from the transfer line 7 but indirectly via the coolant vaporizing duct 13G, the possibility is avoided of liquid gas reaching the coolant circuit when the coolant supply valve 1 is operating intermittently. The reason why may be expressed as follows:

Within the oven 13, the coolant vaporizing duct 13G is coupled to the considerable thermal capacity of the oven, heat being transferred thereto from the physical parts undergoing cooling therein. If we imagine the oven to be at ambient temperature at the start of the cool-down stage and that for a period of one half hour or so before the start no coolant has passed through the transfer line 7 connected to the Dewar, opening the valves 1 and 5 fully for maximum coolant flow does not cause liquid gas to enter the coolant vaporizing duct 13G since during the period when the coolant is static in the transfer line it vaporizes due to ambient heat transfer. If some time thereafter the coolant reaches the upstream end of the coolant vaporizing duct 13G in the liquid state, because the high coolant flow has caused sufficient cooling of the transfer line to prevent vaporization therein, it will have vaporized by the time it reaches the downstream end because of the heat transfer from the oven parts to the coolant flowing in the coolant vaporizing duct 13G, which close to the start of cool-down will be at its maximum.

As the set desired lower temperature is approached and the temperature of the oven parts gets closer to that of the coolant in the coolant vaporizing duct 13G, the coolant absorbs less heat and yet the same maximum flow is being maintained to secure the cool-down rate required. It can well be imagined that, as the set temperature selected is lowered, a point may be reached where the thermal coupling between the coolant vaporizing duct 13G and the oven parts is not sufficient to ensure that any liquid gas arriving at the upstream end of the coolant vaporizing duct 13G is vaporized before it reaches the downstream end. It is therefore a design consideration that the coupling must be adequate to satisfy worst-case situations. In other words, the heat exchanging performance of the coolant vaporizing duct 13G must be sufficient to provide such coupling. This can be achieved in the embodiment of FIG. 5 by selecting the proper length and disposition of the coolant vaporizing duct 13G.

It ought to be mentioned that the coolant vaporizing duct 13G, by absorbing heat from the oven parts, is actually assisting the cooling process by virtue of the fact that it acts as a heat exchanger. The same can be said of course for the runs of coolant supply duct and venting pipe that are led into the oven, said runs being referenced 3C and 11C, respectively, in FIG. 5. This makes for greater efficiency in terms of a lower consumption of liquid gas.

In the embodiment of FIG. 5, the lowest selectable temperature has been fixed at $-100°$ C. by design choice, as in the case of the FIG. 2A and 2C embodiments, but this should not be taken to mean that lower temperatures could not be accommodated. In general, the lowest temperature should be some 20 to 50 degrees higher than the liquefying temperature of the gas used as a coolant, which in the case of nitrogen is $-196°$ C. The volume of the oven 13 is approximately 10,000 cc and its effective thermal capacity is such that it takes approximately 500 watts to raise the temperature of the oven by one degree ° C./sec starting at ambient temperature. The cool-down time from ambient to $-100°$ C. is approximately 6 minutes. It has been found that in such oven a coolant vaporizing duct 13G made up of aluminium tubing having a bore of 7 mm, a wall-thickness of 1.2 mm and a length of 800 mm and disposed as shown in FIG. 5 is adequate in preventing any coolant in the liquid state from reaching the input port of the valve 1 when the oven is fully operational, with the re-circulating fan 13I running, the detector 13F3 and 13F4 initially heated to a temperature of 250° above ambient and the door 13F firmly closed, of course.

It may well be supposed that the coolant vaporizing duct 13G, which towards the end of the cool-down stage may be exposed to an oven temperature close to the lowest selectable value of $-100°$ whilst the coolant flow is still at its maximum, is much less likely to vaporize the coolant from its liquid state than if the same line were exposed to ambient temperature as the transfer line 7 is, but that is not so for a number of reasons. Firstly, the thermal coupling between the transfer line 7 and ambient is very weak, which means that the resistance to heat transfer is quite high and, given sufficient coolant flow, the coolant can readily reach the temperature at which it does not vaporize, almost regardless of what the ambient temperature might be under normal operating conditions, such as are found in a laboratory. Not so, however, in the case of the coolant vaporizing duct 13G which receives heat from the oven parts with which it is in fairly close thermal coupling. At around $-100°$ C., these parts are some 96° C. above the liquefying temperature of nitrogen. It follows that, although line 13G is cooler than $-100°$ C. towards the end of the cool-down stage, any tendency to approach the liquefying temperature of nitrogen will actually result in greater heat transfer thereto from the oven parts. It is important to point out here that heat transfer is assisted by the mixing action of the fan 13I, the normal function of which is to produce a recirculating air stream passing within the coils of the chromatographic column 13F5 and then curling back over the outside of the coils towards the intake side of the fan. When vaporized liquid gas is passed through the oven 13, the same action is available.

Once the critical cool-down stage is over, and valve 5 is mostly closed whilst valve 1 passes a reduced coolant flow, one of the advantages of the two-valve control of the present invention comes to the fore and the likelihood of the coolant being found in the liquid state in the cooling circuit or indeed in the transfer line 7 itself becomes minimal. It is true that occasionally valve 1 and valve 5 are opened together again for short periods, after the temperature control system has settled down for say one half hour or so, to take care of incidental warming up, e.g. of the ambient, but in such case the transfer line 7 is likely to be temporarily warmer than the coolant vaporizing duct 13G and, well before the time it takes for line 7 to cool down sufficiently to allow liquid coolant to pass through, the disturbance is corrected and valve 5 is closed once more, thus preventing further cooling of the transfer line 7. The foregoing is a simplified qualitative analysis of what is believed to be the operation of the FIG. 5 embodiment. A quantitative analysis would be extremely complex and, at all event, unnecessary in the present context.

It should be observed that in FIG. 2A embodiment it was assumed that no significant thermal capacity could be added within the chamber 2D3. This is certainly the case if the adsorption at low temperature of a gas sample within tube 2C is to be followed by a fast thermal desorption cycle which is to raise the tube to an elevated temperature in a few seconds. In the case of a chromatographic oven, added thermal capacity is not so critical since such fast heating cycles are not realistic. The embodiments of FIG. 2A and FIG. 5 deal with different problems. In the first, the emphasis is on close temperature control and avoidance of added thermal capacity; in the second, on adapting the fine temperature control of the first to large-volume cooling while avoiding the presence of liquefied gas in the coolant circuit during intermittent operation of the coolant supply valve 1. Both represent a distinct advancement on the single-valve control of the prior art.

In FIG. 6, the use of liquid gas in the liquid state, as distinct from the vaporized state, is contemplated both during the initial cool-down stage and the next following stage during which the temperature control system tends towards thermal equilibrium while the coolant is being supplied intermittently.

An electrically controllable two-way valve, referenced 1A5 for a reason that will presently be explained, comprises a common input port 1A5A, receiving in operation liquid gas coolant in the liquid state from the transfer line 7 and separate output ports 1A5B and 1A5C, the first communicating with coolant venting pipe 11, having venting orifice 11B and the second with coolant supply duct 3, leading to chamber 2, provided with vent 2A and in-built non-return valve, as described with reference to FIG. 2A. Valve 1A5 is under the automatic control of controller 6, the link L between them symbolizing an electrical connection. The control is such that coolant in the liquid state is flowing continuously from port 1A5A either through a path leading to output port 1A5B (the venting path) or through that leading to output port 1A5C (the supply path), both paths being symbolized by dotted line.

During the initial cool-down of the chamber 2 to the desired lower temperature, the controller 6 activates the supply path and the liquid coolant flows continuously through the chamber and out through the vent 2A, until the chamber or an object therein has reached the desired lower temperature. Thereafter, the operation of the controller is such that the supply path leading to the chamber is operated intermittently, any ON period being determined by the time required for a volume of coolant to flow through the chamber that is sufficient to offset any rise in temperature caused by ambient heat transfer into the chamber. At the end of the aforesaid period the supply path is disabled and the venting path is enabled, the coolant being thus vented through the pipe 11. In other words a flow of coolant is being continuously maintained through one path or the other.

The impedance to flow of the coolant venting pipe 11 and the series combination comprising the coolant supply duct 3, the chamber 2 and the vent 2A are so chosen, if need by a process of trial and error, that the cumulative effect of the coolant flowing intermittently through one and other path is sufficient to prevent the liquid gas ever rising to the vaporizing temperature, with the result that a better temperature control may be achieved compared with the single valve operation of the prior art, wherein incidental vaporization vitiates temperature control for the reasons stated earlier. Again, by controlling both the supply of coolant to the chamber and the venting of the coolant, consumption is markedly reduced. This can readily be appreciated by considering that during the supply phase the venting is cut off altogether. If no provision were made for controlling venting in relation to supplying coolant, venting would have to be maintained-continuously during both the ON and the OFF phases of the coolant supply to the chamber.

FIG. 7 shows how a two-way valve may be readily simulated by means of valve 1 and valve 5 as depicted in FIG. 5, wherein the valves are of identical construction. The ports bearing bases of the two valves are simply joined together in good thermal contact, and the adjacent input ports 1A and 5A are manifolded together by manifold M, to which is also connected the transfer line 7. The reason for using the reference 1A5 (suggesting: 1 and 5) in FIG. 6 will now be apparent. In practical terms, the simulation may be more expedient than a single valve designed as a two-way valve, which may not be readily available for use at cryogenic temperatures.

The controller shown in FIG. 6 and FIG. 7 (in the latter the electrical leads from valves 1 and 5, respectively, to the controller 6 are symbolized by LL1 and LL2) is identical with the one described in FIG. 3, except that the software conditioning the microcomputer 6C implements different commands, as shown in the flow chart of FIG. 8. In both figures a temperature sensor 2B within the chamber 2 feeds into the controller 6 as in FIGS. 1 and 2.

In FIG. 8, steps 14A, 14B and 14C conform to the first three steps in FIG. 4. At 14D the microcomputer forming part of controller 6 is conditioned to enable the supply path of the two-way valve 1A5 of FIG. 6 and to keep the venting path disabled, thus initiating the cool-down stage of the chamber 2. The waiting loop represented at 14E ensures that the cool-down continues as long as the temperature is higher than the desired lower temperature −X, the minus sign having the same meaning as defined with reference to the flow chart of FIG. 4. 14F is another waiting loop to keep the cool-down on until the actual temperature is some 1.5° C. below the desired lower temperature, when the supply path (SP) of valve 1A5 is closed and the venting path (VP) is opened as indicated at 14G. Finally, the waiting loop of 14H maintains the two-way valve 1A5 in the condition stated at 14G for as long as the actual temperature is some 10° C. below the desired lower value. If the temperature rises above −(X+10), the entire control operation starting from 14D is reiterated.

When the system of FIG. 6 is first put into operation, the coolant will pass through the valve 1A5 and the remainder of the coolant circuit in the vaporized state. However, coolant flowing to atmosphere alternately via the chamber 2 and the venting pipe 11 will soon ensure that vaporized coolant is replaced by liquefied coolant within the coolant circuit.

It will be noted that the temperature control is not as close as when the desired lower temperature is sufficiently high to enable vaporized coolant to be used. This is largely due to the fact the temperature of liquid gas in the liquid state varies within a very short range compared with that of vaporized liquid gas. This is a main reason why temperature control by vaporized coolant is preferable, in accordance with the present invention, where extreme desired lower temperatures are not involved.

The control of the two-way valve 1A5 as described hereabove equally applies, mutatis mutandis, to the simulation of FIG. 7.

What is claimed is:

1. A temperature control system for lowering the temperature within a chamber from a higher actual value to a desired lower value and maintaining it at said desired lower value by passing through the chamber a controlled flow of coolant available from a source of supply in the form of liquid gas, comprising:
   a) a chamber adapted to allow a flow of coolant therethrough;
   b) means for defining a coolant venting orifice;
   c) means for automatically selectively supplying coolant to the chamber and the coolant venting orifice along parallel coolant flow paths;
   d) a temperature sensor located within the chamber;
   e) a temperature setting means for setting the desired lower temperature;
   f) a controller including means for storing and executing a sequence of operational instructions, said controller coordinating in operation coolant flow through the venting orifice, via one of said parallel flow paths with that through the chamber, via the other of said parallel flow paths by controlling the means for automatically selectively supplying the coolant in accordance with said instructions and in response to the temperature sensor and the temperature setting means, whereby the chamber and/or any object therein is brought to and maintained at the set desired lower value.

2. A temperature control system as claimed in claim 1, wherein the controller is adapted to control in operation the said means for automatically selectively supplying coolant to route coolant simultaneously to the chamber and the coolant venting orifice at a predeterminedly high cumulative flow rate to achieve an initial cooldown of the chamber and/or any object therein to the set desired lower temperature value in as short a time as required, within the practical limits of the system.

3. A temperature control system as claimed in claim 2, wherein the controller is adapted to control in operation the means for automatically selectively supplying coolant to introduce, upon cool-down to the desired lower temperature value being completed, timed intermittence of coolant flow through the chamber, and, where a higher rate of cooling is momentarily required, through both the chamber and the venting orifice until a steady state stage is reached at which the controller is adapted to cut off the supply of coolant through the venting orifice, except for brief occasional periods when incidental temperature rises such as due to ambient disturbances must be counteracted, and to maintain the set temperature by controlling the frequency and/or the duration of the flow through the chamber, the frequency and/or the duration tending to decrease.

4. A temperature control system as claimed in claim 1, wherein the means for automatically selectively supplying coolant to the chamber and the coolant venting orifice comprise electrically controllable coolant supply valve and coolant venting valve, each having an input port and an output port.

5. A system as claimed in claim 4, wherein the controller includes a microcomputer arranged to compare in operation a signal representing the actual temperature of the chamber and/or any object therein as sensed by the temperature sensor with the desired lower temperature value set by the operator via the temperature setting means and to control the operation of the coolant supply valve and the coolant venting valve in accordance with a software program accessible to the microcomputer.

6. A system as claimed in claim 5, wherein the input port of the coolant supply valve is arranged for receiving coolant from a coolant source via a transfer line and the output port is connected to a coolant supply duct for conveying coolant to the chamber.

7. A system as claimed in claim 6, wherein the coolant supply valve is additionally connected to a coolant venting duct feeding into the input port of the coolant venting valve, the output port of which constitutes or leads to the coolant venting orifice.

8. A system as claimed in claim 7, wherein the controller is adapted to cause the coolant supply valve and the coolant venting valve to be conditioned for near maximum predetermined coolant flow therethrough during an initial cool-down of the chamber to the set desired lower value.

9. A system as claimed in claim 81 wherein the controller is adapted to cause intermittent operation of both the coolant supply valve and the cooling venting valve after the set desired temperature has been reached at the end of cool-down and the system has entered into a settling down stage, the coolant supply valve being predominantly operative during the said stage and the coolant venting valve being opened momentarily to secure occasional extra cooling, if and when required to counteract prominent temperature rise trends.

10. A system as claimed in claim 9, wherein the controller is further adapted to lengthen the intervals during which the coolant supply valve is inoperative and to render the intervention of the cooling venting valve less and less frequent as the system tends to converge towards a steady state.

11. A system as claimed in claim 1, wherein the chamber houses an object to be cooled which is thermally coupled to a thermo-electric cooling device, the system being adapted to provide overriding cooling when the desired lower temperature value is outside the range of said cooling device.

12. A system as claimed in claim 11, wherein the object is a cold trap hollow body.

13. A system as claimed i-n claim 12, wherein the hollow body is a tube surrounded by a jacket and the chamber has a small volume of a few cubic centimeters defined in the interspace.

14. A system as claimed in claim 13, wherein the jacket is surround by an ante-chamber far exceeding the volumetric capacity of the chamber, the ante-chamber being provided with a valved vent that opens to atmosphere under predetermined coolant positive pressure.

15. A system as claimed in claim 14, wherein the chamber and the ante-chamber are so arranged that in operation coolant flow will first be admitted to the chamber, then from the chamber to the ante-chamber and finally to atmosphere via the said vent.

16. A system as claimed in claim 1, wherein the chamber forms a substantially gas-tight enclosure except for a valved vent that opens to atmosphere when subjected to a predetermined positive coolant pressure.

17. A system as claimed in claim 1, wherein the chamber houses a coolant vaporizing duct adapted to be connected to a transfer line at one end and connected to the means for automatically selectively supplying coolant to the chamber and the venting orifice at the other end.

18. A system as claimed in claim 17, wherein the venting orifice is within the chamber itself.

19. A system as claimed in claims 17, wherein the chamber constitutes a gas chromatographic oven.

20. A system as claimed in claim 1, wherein the impedance to flow encountered by the coolant and the control exerted by the controller on the means for automatically selectively supplying coolant to the chamber and the venting orifice are so chosen that the coolant enters and leaves the said means in the vaporized state only.

21. A system as claimed in claim 1, wherein the means for automatically selectively supplying coolant to the chamber and the venting orifice comprise a two-way electrically controlled valve for routing liquid coolant from a transfer line either to the chamber or to the venting orifice, but not both at the same time.

22. A system as claimed in claim 21, wherein the controller includes a microcomputer arranged to compare in operation a signal representing the actual temperature of the chamber and/or any object therein as sensed by the temperature sensor with the desired lower temperature value set by the operator via the temperature setting means and to control the operation of the two-way valve in accordance with a software program accessible to the microcomputer.

23. A system as claimed in claim 22, wherein the microcomputer is conditioned to switch the two-way valve so as to cause coolant to flow only through the chamber during an initial fast cool-down.

24. A system as claimed in claim 23, wherein the microcomputer is so conditioned that after the cool-down has taken place it will cause the two-way valve to switch intermittently between the chamber and the venting orifice so as to supply coolant to the chamber at such frequency as may be required to offset any heat transfer to the chamber tending to raise the temperature thereof above the set desired lower temperature and at the same time prevent the coolant from vaporizing when the flow of coolant to the chamber is cut off.

25. A system as claimed in claim 21, wherein the two-way valve is represented by two identical solenoid valves with their bases in good thermal contact and the two input ports linked so that they may be fed in parallel from a transfer line.

26. A method of temperature control for lowering the temperature within a chamber from a higher actual value to a desired lower value and maintaining it at said desired lower value by passing through the chamber a controlled flow of coolant available from a source of supply in the form of liquid gas, comprising the steps of:
 a) sensing the temperature within the chamber;
 b) coordinating, in accordance with a stored sequence of operational instructions responding to the sensed chamber temperature and a desired lower value, the flow of coolant through a venting orifice with that through the chamber along parallel flow paths in first attaining said desired lower value and then maintaining it for a required period of use.

27. A method as claimed in claim 26, wherein the said sequence of instructions include provision for maintaining a predeterminedly high flow of coolant through both the chamber and the venting orifice during an initial cool-down period in first attaining said desired lower value.

28. A method as claimed in claim 27, wherein a timed intermittence of coolant flow through the chamber and the venting orifice selectively is introduced during a settling down period in which temperature control is exerted mainly by intermittently causing coolant to flow through the chamber in response to chamber temperature whilst the flow through the venting orifice is cut off and less frequently by momentarily allowing coolant to flow through the venting orifice simultaneously with the occurrence of flow through the chamber, when extra cooling is called for.

29. A method as claimed in claim 28, wherein as the temperature control approaches the steady state temperature control is exerted almost entirely by intermittently allowing coolant flow through the chamber so that the no-flow intervals become longer and longer whilst coolant flow through the venting orifice is cut off and only occasionally reintroduced to combat incidental temperature surges such as might be due to ambient temperature peaks.

30. A method as claimed in claim 29, wherein coolant flow through the chamber and the venting orifice, respectively, is selectively controlled via a microcomputer responsive to a software program.

31. A method as claimed in claim 26, when applied to lowering the temperature of a cold trap for the purpose of condensing on an adsorbent located therein a sample entrained in a carrier gas flowing through the trap.

32. A method as claimed in claim 31, wherein the temperature of a cold trap is lowered within a range having a sub-zero limit by a thermo-electric method and lower down by superimposing on it the method of claim 31.

33. A method as claimed in claim 31, further comprising the step of desorbing the sample into a gas chromatographic column by raising the temperature of the trap rapidly to the requisite level.

34. A method as claimed in claim 31, wherein regulation of coolant flow through the chamber and the venting orifice, respectively, is so arranged that the coolant being regulated and admitted to the chamber and the venting orifice is in the vaporized state only.

35. A method as claimed in claim 26, when applied to lowering the temperature of a gas chromatographic oven.

36. A method as claimed in claim 35, wherein a predetermined heat exchange is established between the inflowing coolant and the oven before the flow of coolant is regulated selectively through the oven and the venting orifice in order to prevent the coolant from undergoing regulation in the liquefied state.

37. A method as claimed in claim 26, wherein a predeterminedly high flow of coolant in the liquid state is maintained through the chamber one during an initial cool-down period in first attaining said desired lower value.

38. A method as claimed in claim 37, wherein the coolant flow is made to alternate between the chamber and the venting orifice after the initial cool-down has taken place.

39. A method as claimed in claim 38, including the step of regulating coolant flow through an electrically operated two-way valve controlled by a microcomputer responsive to a computer program.

* * * * *